(12) United States Patent
Kontermann et al.

(10) Patent No.: US 8,859,739 B2
(45) Date of Patent: Oct. 14, 2014

(54) ANTI-HUTNFR1 ANTIBODY AND METHODS OF USE THEREOF FOR TREATMENT

(75) Inventors: Roland Kontermann, Nurtingen (DE); Klaus Pfizenmaier, Tiefenbronn (DE); Andreas Herrmann, Pfeffingen (CH); Kirstin Zettlitz, Sherman Oaks, CA (US)

(73) Assignee: Baliopharm AG, Basel (CH)

( * ) Notice: Subject to any disclaimer, the term of this patent is extended or adjusted under 35 U.S.C. 154(b) by 0 days.

(21) Appl. No.: 13/823,008

(22) PCT Filed: Sep. 16, 2011

(86) PCT No.: PCT/EP2011/066109
§ 371 (c)(1),
(2), (4) Date: May 20, 2013

(87) PCT Pub. No.: WO2012/035141
PCT Pub. Date: Mar. 22, 2012

(65) Prior Publication Data
US 2013/0251707 A1    Sep. 26, 2013

(30) Foreign Application Priority Data
Sep. 16, 2010  (EP) ..................................... 10177080

(51) Int. Cl.
*C12P 21/08* (2006.01)
*A61K 39/00* (2006.01)
*A61K 39/395* (2006.01)
*C07K 16/28* (2006.01)

(52) U.S. Cl.
CPC ......... *C07K 16/2866* (2013.01); *C07K 2317/41* (2013.01); *C07K 2317/56* (2013.01); *C07K 16/2878* (2013.01); *C07K 2317/76* (2013.01); *C07K 2317/24* (2013.01); *C07K 2317/92* (2013.01); *C07K 2317/71* (2013.01)
USPC ................... 530/387.3; 424/133.1; 424/172.1

(58) Field of Classification Search
CPC ........... C07K 16/2866; C07K 2316/52; C07K 2316/96; C07K 2317/71; C07K 2317/24
See application file for complete search history.

(56) References Cited

U.S. PATENT DOCUMENTS
5,736,138 A    4/1998    Pfizenmaier et al.

FOREIGN PATENT DOCUMENTS
WO    WO/2006/038027    8/2006
WO    WO/2008/113515    9/2008
WO    WO/2008/149148    12/2008
WO    WO/2010/094720    8/2010

OTHER PUBLICATIONS

An Z, et al. mAbs, 1(6):572-579, 2009 (onliune at www.landesbioscience.com/journals/mabs/article/10185.*
International Search Report, International Patent Application No. PCT/EP2011/066109, Nov. 22, 2011.
International Written Opinion, International Patent Application No. PCT/EP2011/066109, Nov. 22, 2011.
International Preliminary Report on Patentability, International Patent Application No. PCT/EP2011/066109, Mar. 19, 2013.
Extended European Search Report, European Patent Application No. 10177080.8, Jan. 24, 2011.
Armour et al., European Jounal of Immunology 29(8):2613-2624 (1999).
Brocks et al., Immunotechnology, 3(3):173-184 (1997).
Espevik T et al., J. Exp. Med., 1990, 171:415-426.
Hellendoorn et al., Cancer Cell International, 2004, 4 (Sppl. I): 20.
Hwang W Y et al., Methods, 2005, 36:35-42.
InvivoGen: "IgG—Fc engineering for therapeutic use," 2007, pp. 1-2, XP002616317.
Jones P T et al., Nature, 1986, 321:522-525.
Kashmiri S V et al., Methods, 2005, 36:25-34.
Krippner-Heidenreich A. et al., J. Biol. Chem., 277(46):44155-44163 (2002).
Lifely M R et al., Glycobiology, 5:813-822 (1995).
Locksley et al., Cell., 2001, 104(4):487-501.
Moosmayer D et al., Ther Immunol., 1995, 2(1):31-40.
Müller D et al., J. Biol. Chem, 282(17):12650-12660 (2007).
Müller D et al., J. Immunol. Methods, 339(1):90-98 (2008).
Olleros M L et al., J Infect Dis., 2009, 199(7):1053-1063.
Roguska M A et al., Proc. Natl. Acad. Sci. USA, 1994, 91:969-973.
Shibata H et al., Cytokine, 2008, 44(2):229-233.
Shields R L et al., J Biol Chem., 2001, 276(9):6591-6604.
Oganesyan Vaheh et al., Acta Crystallographica Section D: Biological Crystallography, Munksgaard Publishers Ltd. Copenhagen, DK, vol. 64, No. 6, pp. 700-704 (2008).
Kontermann Roland E et al., Journal of Immunotherapy: With Emphasis on Tumor Immunology, Raven Press, US, vol. 31, No. 3, pp. 225-234 (2008).

* cited by examiner

*Primary Examiner* — Robert Landsman
(74) *Attorney, Agent, or Firm* — Michael Fedrick; Loza & Loza, LLP

(57) ABSTRACT

The disclosure to an anti-huTNFR1 antibody of the IgG1 type, which has a modified Fc region deficient in mediating effector function, a pharmaceutical preparation comprising such antibody, and an anti-huTNFR1 antibody of the IgG1 type for use as a TNF antagonist without forming an agonistic TNFR1 signalling complex, as an alternative to treatment with an anti-TNF therapeutic.

16 Claims, 12 Drawing Sheets

Fig. 8 a)

Figure 1:
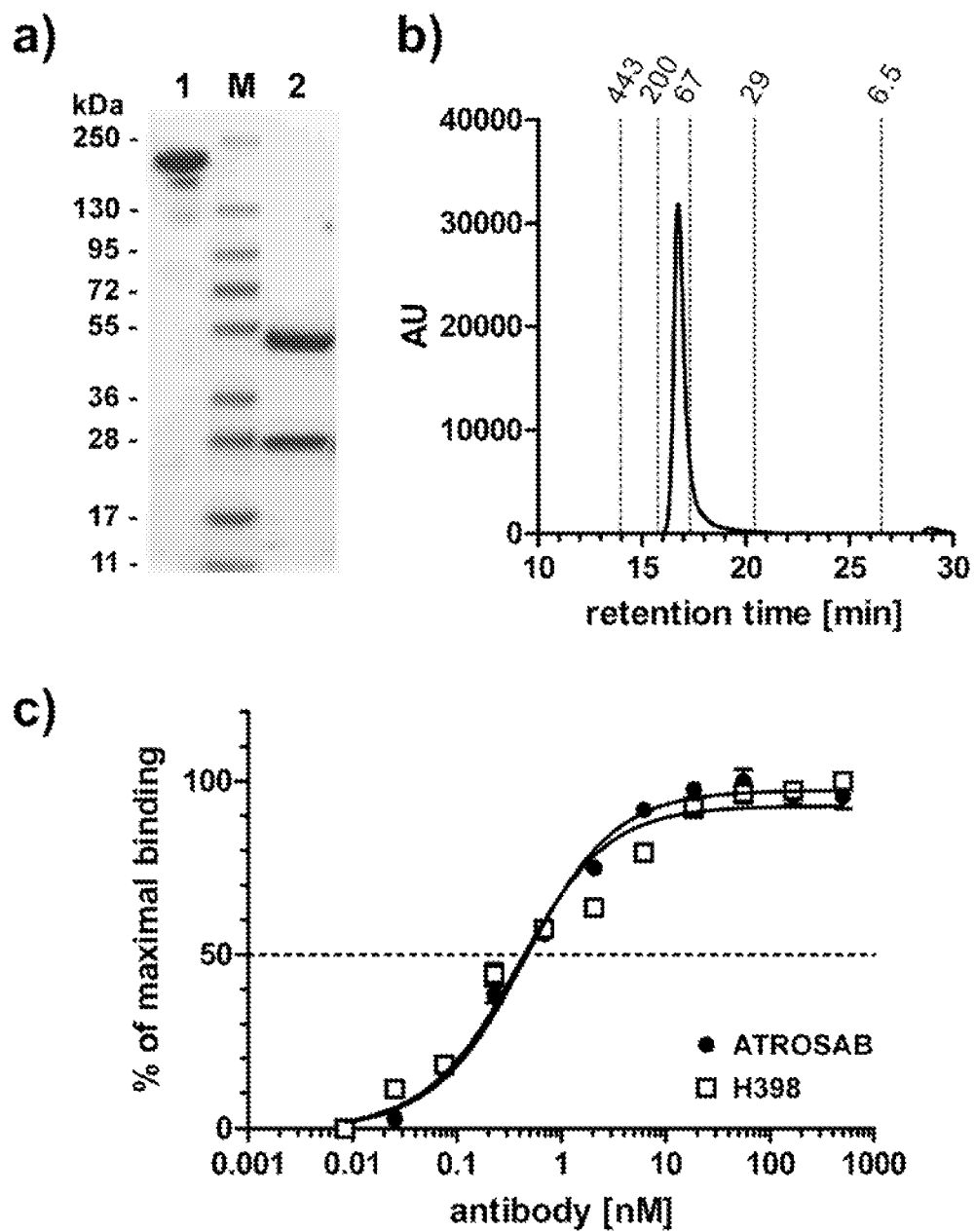

| # | | CRD1 (1-29, 29-53) | CRD2 (53-71, 71-96) | CRD3 (96-137) | CRD4 (137-175) | H398 | IZI-06.1 | huTNF |
|---|---|---|---|---|---|---|---|---|
| 1 | huTNFR1 | A1 / B2 | A1 / B2 | ■ | ■ | +++ | +++ | +++ |
| 2 | moTNFR1 | □ / □ | □ / □ | □ | □ | − | − | +++ |
| 3 | TNFR1 m12/h34 | □ / □ | □ / □ | ■ | ■ | (+) | − | ++ |
| 4 | TNFR1 m1/h2-4 | □ / □ | ■ / ■ | ■ | ■ | − | − | + |
| 5 | TNFR1 m1A1/h1B2-4 | □ / ■ | ■ / ■ | ■ | ■ | (+) | − | +++ |
| 6 | TNFR1 h1A1/m1B2-4 | ■ / □ | □ / □ | □ | □ | − | − | +++ |
| 7 | TNFR1 h1/m2-4 | ■ / ■ | □ / □ | □ | □ | (+) | (+) | +++ |
| 8 | TNFR1 h1-2A1/m2B2-4 | ■ / ■ | ■ / □ | □ | □ | +++ | +++ | +++ |
| 9 | TNFR1 h12/m34 | ■ / ■ | ■ / ■ | □ | □ | +++ | +++ | +++ |
| 10 | TNFR1 h1-2A1/m2B2-4 P23S,Q24K | ■ / ■ | ■ / □ | □ | □ | − | − | +++ | b)

```
                  |     CRD1-A1      |     CRD1-B2                         |     CRD2-A1
huTNFR1   LVPHLGDREKR DSVCPQGKYIHPQNNSICCTKCHKGTYLYNDCPGPGQDTDCR ECESGSFTASENHLRHC
moTNFR1   ---S------- --L------V-SK---------------VS---S--R--V-- ---K-T----Q-Y--Q-
rhTNFR1   ----------- -----------V---------------------------------- -----------------
```

Fig 9

Fig. 9 a)
QVQLVQSGAEVKKPGSSVKVSCKASGYTFTDFYINWVRQAPGQGLEWIGEIYPYSG
HAYYNEKFKARVTITADKSTSTAYMELSSLRSEDTAVYYCARWDFLDYWGQGTTVTV
SSASTKGPSVFPLAPSSKSTSGGTAALGCLVKDYFPEPVTVSWNSGALTSGVHTFPA
VLQSSGLYSLSSVVTVPSSSLGTQTYICNVNHKPSNTKVDKKVEPKSCDKTHTCPPC
PAPPVAGPSVFLFPPKPKDTLMISRTPEVTCVVVDVSHEDPEVKFNWYVDGVEVHNA
KTKPREEQYNSTYRVVSVLTVLHQDWLNGKEYKCKVSNKGLPSSIEKTISKAKGQPR
EPQVYTLPPSRDELTKNQVSLTCLVKGFYPSDIAVEWESNGQPENNYKTTPPVLDSD
GSFFLYSKLTVDKSRWQQGNVFSCSVMHEALHNHYTQKSLSLSPGK

Fig. 9 b)
QVQLVQSGAEVKKPGSSVKVSCKASGYTFTDFYINWVRQAPGQGLEWIGEIYPYSG
HAYYNEKFKARVTITADKSTSTAYMELSSLRSEDTAVYYCARWDFLDYWGQGTTVTV
SS

Fig. 9 c)
ASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKKVEPKSC

Fig. 9 d)
DKTHTCPPCPAPPVAG

Fig. 9 e)
PSVFLFPPKPKDTLMISRTPEVTCVVVDVSHEDPEVKFNWYVDGVEVHNAKTKPREE
QYNSTYRVVSVLTVLHQDWLNGKEYKCKVSNKGLPSSIEKTISKAK

Fig. 9 f)
GQPREPQVYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPGK

Fig. 9 g)

DIVMTQSPLSLPVTPGEPASISCRSSQSLLHSNGNTYLHWYLQKPGQSPQLLIYTVSN
RFSGVPDRFSGSGSGTDFTLKISRVEAEDVGVYYCSQSTHVPYTFGGGTKVEIKRTV
AAPSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGEC

Fig. 9 h)

DIVMTQSPLSLPVTPGEPASISCRSSQSLLHSNGNTYLHWYLQKPGQSPQLLIYTVSN
RFSGVPDRFSGSGSGTDFTLKISRVEAEDVGVYYCSQSTHVPYTFGGGTKVEIKR

Fig 9 i)

TVAAPSVFIFPPSDEQLKSGTASVVCLLNNFYPREAKVQWKVDNALQSGNSQESVTE
QDSKDSTYSLSSTLTLSKADYEKHKVYACEVTHQGLSSPVTKSFNRGEC

Fig. 10:

SEQ ID NO.: 1

Gly Tyr Thr Phe Thr Asp Phe Tyr Ile Asn

SEQ ID NO.: 2

Trp Ile Gly Glu Ile Tyr Pro Tyr Ser Gly His Ala Tyr Tyr Asn Glu Lys Phe Lys Ala

SEQ ID NO.: 3

Trp Asp Phe Leu Asp Tyr

SEQ ID NO.: 4

Arg Ser Ser Gln Ser Leu Leu His Ser Asn Gly Asn Thr Tyr Leu His Trp Tyr

SEQ ID NO.: 5

Leu Leu Ile Tyr Thr Val Ser Asn Arg Phe Ser

SEQ ID NO.: 6

Ser Gln Ser Thr His Val Pro Tyr Thr

SEQ ID NO.: 7

Gln Val Gln Leu Val Gln Ser Gly Ala Glu Val Lys Lys Pro Gly Ser Ser Val Lys Val Ser Cys Lys Ala Ser Gly Tyr Thr Phe Thr Asp Phe Tyr Ile Asn Trp Val Arg Gln Ala Pro Gly Gln Gly Leu Glu Trp Ile Gly Glu Ile Tyr Pro Tyr Ser Gly His Ala Tyr Tyr Asn Glu Lys Phe Lys Ala Arg Val Thr Ile Thr Ala Asp Lys Ser Thr Ser Thr Ala Tyr Met Glu Leu Ser Ser Leu Arg Ser Glu Asp Thr Ala Val Tyr Tyr Cys Ala Arg Trp Asp Phe Lleu Asp Tyr Trp Gly Gln Gly Thr Thr Val Thr Val Ser Ser

SEQ ID NO.: 8

Asp Ile Val Met Thr Gln Ser Pro Leu Ser Leu Pro Val Thr Pro Gly Glu Pro Ala Ser Ile Ser Cys Arg Ser Ser Gln Ser Leu Leu His Ser Asn Gly Asn Thr Tyr Leu His Trp Tyr Leu Gln Lys Pro Gly Gln Ser Pro Gln Leu Leu Ile Tyr Thr Val Ser Asn Arg Phe Ser Gly Val Pro Asp Arg Phe Ser Gly Ser Gly Ser Gly Thr Asp Phe Thr Leu Lys Ile Ser Arg Val Glu Ala Glu Asp Val Gly Val Tyr Tyr Cys Ser Gln Ser Thr His Val Pro Tyr Thr Phe Gly Gly Gly Thr Lys Val Glu Ile Lys Arg

SEQUENCE LISTING

```
<160> NUMBER OF SEQ ID NOS: 19

<210> SEQ ID NO 1
<211> LENGTH: 10
<212> TYPE: PRT
<213> ORGANISM: Artificial Sequence
<220> FEATURE:
<223> OTHER INFORMATION: CDR sequence

<400> SEQUENCE: 1

Gly Tyr Thr Phe Thr Asp Phe Tyr Ile Asn
1               5                   10

<210> SEQ ID NO 2
<211> LENGTH: 20
<212> TYPE: PRT
<213> ORGANISM: Artificial Sequence
<220> FEATURE:
<223> OTHER INFORMATION: CDR sequence

<400> SEQUENCE: 2

Trp Ile Gly Glu Ile Tyr Pro Tyr Ser Gly His Ala Tyr Tyr Asn Glu
1               5                   10                  15

Lys Phe Lys Ala
            20

<210> SEQ ID NO 3
<211> LENGTH: 6
<212> TYPE: PRT
<213> ORGANISM: Artificial Sequence
<220> FEATURE:
<223> OTHER INFORMATION: CDR sequence

<400> SEQUENCE: 3

Trp Asp Phe Leu Asp Tyr
1               5

<210> SEQ ID NO 4
<211> LENGTH: 18
<212> TYPE: PRT
<213> ORGANISM: Artificial Sequence
<220> FEATURE:
<223> OTHER INFORMATION: CDR sequence

<400> SEQUENCE: 4

Arg Ser Ser Gln Ser Leu Leu His Ser Asn Gly Asn Thr Tyr Leu His
1               5                   10                  15
```

Trp Tyr

<210> SEQ ID NO 5
<211> LENGTH: 11
<212> TYPE: PRT
<213> ORGANISM: Artificial Sequence
<220> FEATURE:
<223> OTHER INFORMATION: CDR sequence

<400> SEQUENCE: 5

Leu Leu Ile Tyr Thr Val Ser Asn Arg Phe Ser
1               5                   10

<210> SEQ ID NO 6
<211> LENGTH: 9
<212> TYPE: PRT
<213> ORGANISM: Artificial Sequence
<220> FEATURE:
<223> OTHER INFORMATION: CDR sequence

<400> SEQUENCE: 6

Ser Gln Ser Thr His Val Pro Tyr Thr
1               5

<210> SEQ ID NO 7
<211> LENGTH: 115
<212> TYPE: PRT
<213> ORGANISM: Artificial Sequence
<220> FEATURE:
<223> OTHER INFORMATION: VH

<400> SEQUENCE: 7

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Phe
                20                  25                  30

Tyr Ile Asn Trp Val Arg Gln Ala Pro Gly Gln Gly Leu Glu Trp Ile
            35                  40                  45

Gly Glu Ile Tyr Pro Tyr Ser Gly His Ala Tyr Tyr Asn Glu Lys Phe
        50                  55                  60

Lys Ala Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Asp Phe Leu Asp Tyr Trp Gly Gln Gly Thr Thr Val Thr
            100                 105                 110

Val Ser Ser
        115

<210> SEQ ID NO 8
<211> LENGTH: 113
<212> TYPE: PRT
<213> ORGANISM: Artificial Sequence
<220> FEATURE:
<223> OTHER INFORMATION: VL

<400> SEQUENCE: 8

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Asn Thr Tyr Leu His Trp Tyr Leu Gln Lys Pro Gly Gln Ser

-continued

```
                35                  40                  45
Pro Gln Leu Leu Ile Tyr Thr Val Ser Asn Arg Phe Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gly Gly Thr Lys Val Glu Ile Lys
               100                 105                 110

Arg
```

<210> SEQ ID NO 9
<211> LENGTH: 223
<212> TYPE: PRT
<213> ORGANISM: human

<400> SEQUENCE: 9

```
Thr Cys Pro Pro Cys Pro Ala Pro Glu Leu Leu Gly Gly Pro Ser Val
  1               5                  10                  15

Phe Leu Phe Pro Pro Lys Pro Lys Asp Thr Leu Met Ile Ser Arg Thr
                 20                  25                  30

Pro Glu Val Thr Cys Val Val Val Asp Val Ser His Glu Asp Pro Glu
                35                  40                  45

Val Lys Phe Asn Trp Tyr Val Asp Gly Val Glu Val His Asn Ala Lys
        50                  55                  60

Thr Lys Pro Arg Glu Glu Gln Tyr Asn Ser Thr Tyr Arg Val Val Ser
 65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
               100                 105                 110

Ser Lys Ala Lys Gly Gln Pro Arg Glu Pro Gln Val Tyr Thr Leu Pro
               115                 120                 125

Pro Ser Arg Asp Glu Leu Thr Lys Asn Gln Val Ser Leu Thr Cys Leu
               130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
               165                 170                 175

Asp Gly Ser Phe Phe Leu Tyr Ser Lys Leu Thr Val Asp Lys Ser Arg
               180                 185                 190

Trp Gln Gln Gly Asn Val Phe Ser Cys Ser Val Met His Glu Ala Leu
               195                 200                 205

His Asn His Tyr Thr Gln Lys Ser Leu Ser Leu Ser Pro Gly Lys
               210                 215                 220
```

<210> SEQ ID NO 10
<211> LENGTH: 444
<212> TYPE: PRT
<213> ORGANISM: Artificial Sequence
<220> FEATURE:
<223> OTHER INFORMATION: heavy chain

<400> SEQUENCE: 10

```
Gln Val Gln Leu Val Gln Ser Gly Ala Glu Val Lys Lys Pro Gly Ser
  1               5                  10                  15
```

```
Ser Val Lys Val Ser Cys Lys Ala Ser Gly Tyr Thr Phe Thr Asp Phe
             20                  25                  30

Tyr Ile Asn Trp Val Arg Gln Ala Pro Gly Gln Gly Leu Glu Trp Ile
         35                  40                  45

Gly Glu Ile Tyr Pro Tyr Ser Gly His Ala Tyr Tyr Asn Glu Lys Phe
     50                  55                  60

Lys Ala Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                 85                  90                  95

Ala Arg Trp Asp Phe Leu Asp Tyr Trp Gly Gln Gly Thr Thr Val Thr
             100                 105                 110

Val Ser Ser Ala Ser Thr Lys Gly Pro Ser Val Phe Pro Leu Ala Pro
         115                 120                 125

Ser Ser Lys Ser Thr Ser Gly Gly Thr Ala Ala Leu Gly Cys Leu Val
     130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                 165                 170                 175

Leu Tyr Ser Leu Ser Ser Val Val Thr Val Pro Ser Ser Ser Leu Gly
             180                 185                 190

Thr Gln Thr Tyr Ile Cys Asn Val Asn His Lys Pro Ser Asn Thr Lys
         195                 200                 205

Val Asp Lys Lys Val Glu Pro Lys Ser Cys Asp Lys Thr His Thr Cys
210                 215                 220

Pro Pro Cys Pro Ala Pro Val Ala Gly Pro Ser Val Phe Leu Phe
225                 230                 235                 240

Pro Pro Lys Pro Lys Asp Thr Leu Met Ile Ser Arg Thr Pro Glu Val
                 245                 250                 255

Thr Cys Val Val Val Asp Val Ser His Glu Asp Pro Glu Val Lys Phe
             260                 265                 270

Asn Trp Tyr Val Asp Gly Val Glu Val His Asn Ala Lys Thr Lys Pro
         275                 280                 285

Arg Glu Glu Gln Tyr Asn Ser Thr Tyr Arg Val Val Ser Val Leu Thr
     290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                 325                 330                 335

Lys Gly Gln Pro Arg Glu Pro Gln Val Tyr Thr Leu Pro Pro Ser Arg
             340                 345                 350

Asp Glu Leu Thr Lys Asn Gln Val Ser Leu Thr Cys Leu Val Lys Gly
         355                 360                 365

Phe Tyr Pro Ser Asp Ile Ala Val Glu Trp Ser Asn Gly Gln Pro
     370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                 405                 410                 415

Gly Asn Val Phe Ser Cys Ser Val Met His Glu Ala Leu His Asn His
             420                 425                 430

Tyr Thr Gln Lys Ser Leu Ser Leu Ser Pro Gly Lys
```

-continued

```
        435             440
```

<210> SEQ ID NO 11
<211> LENGTH: 115
<212> TYPE: PRT
<213> ORGANISM: Artificial Sequence
<220> FEATURE:
<223> OTHER INFORMATION: VH

<400> SEQUENCE: 11

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Phe
            20                  25                  30

Tyr Ile Asn Trp Val Arg Gln Ala Pro Gly Gln Gly Leu Glu Trp Ile
        35                  40                  45

Gly Glu Ile Tyr Pro Tyr Ser Gly His Ala Tyr Tyr Asn Glu Lys Phe
    50                  55                  60

Lys Ala Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Asp Phe Leu Asp Tyr Trp Gly Gln Gly Thr Thr Val Thr
            100                 105                 110

Val Ser Ser
        115

<210> SEQ ID NO 12
<211> LENGTH: 103
<212> TYPE: PRT
<213> ORGANISM: Artificial Sequence
<220> FEATURE:
<223> OTHER INFORMATION: CH1

<400> SEQUENCE: 12

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100

<210> SEQ ID NO 13
<211> LENGTH: 16
<212> TYPE: PRT
<213> ORGANISM: Artificial Sequence
<220> FEATURE:
<223> OTHER INFORMATION: hinge sequence

<400> SEQUENCE: 13

Asp Lys Thr His Thr Cys Pro Pro Cys Pro Ala Pro Pro Val Ala Gly
1               5                   10                  15

```
<210> SEQ ID NO 14
<211> LENGTH: 103
<212> TYPE: PRT
<213> ORGANISM: Artificial Sequence
<220> FEATURE:
<223> OTHER INFORMATION: CH2

<400> SEQUENCE: 14

Pro Ser Val Phe Leu Phe Pro Pro Lys Pro Lys Asp Thr Leu Met Ile
1               5                   10                  15

Ser Arg Thr Pro Glu Val Thr Cys Val Val Val Asp Val Ser His Glu
            20                  25                  30

Asp Pro Glu Val Lys Phe Asn Trp Tyr Val Asp Gly Val Glu Val His
        35                  40                  45

Asn Ala Lys Thr Lys Pro Arg Glu Glu Gln Tyr Asn Ser Thr Tyr Arg
50                  55                  60

Val Val Ser Val Leu Thr Val Leu His Gln Asp Trp Leu Asn Gly Lys
65                  70                  75                  80

Glu Tyr Lys Cys Lys Val Ser Asn Lys Gly Leu Pro Ser Ser Ile Glu
            85                  90                  95

Lys Thr Ile Ser Lys Ala Lys
            100

<210> SEQ ID NO 15
<211> LENGTH: 107
<212> TYPE: PRT
<213> ORGANISM: Artificial Sequence
<220> FEATURE:
<223> OTHER INFORMATION: CH3

<400> SEQUENCE: 15

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
            85                  90                  95

Thr Gln Lys Ser Leu Ser Leu Ser Pro Gly Lys
            100                 105

<210> SEQ ID NO 16
<211> LENGTH: 219
<212> TYPE: PRT
<213> ORGANISM: Artificial Sequence
<220> FEATURE:
<223> OTHER INFORMATION: light chain

<400> SEQUENCE: 16

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30
```

```
Asn Gly Asn Thr Tyr Leu His Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 17
<211> LENGTH: 113
<212> TYPE: PRT
<213> ORGANISM: Artificial Sequence
<220> FEATURE:
<223> OTHER INFORMATION: VL

<400> SEQUENCE: 17

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gly Gly Thr Lys Val Glu Ile Lys
            100                 105                 110

Arg

<210> SEQ ID NO 18
<211> LENGTH: 106
<212> TYPE: PRT
<213> ORGANISM: Artificial Sequence
<220> FEATURE:
<223> OTHER INFORMATION: CL

<400> SEQUENCE: 18
```

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
        50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 19
<211> LENGTH: 70
<212> TYPE: PRT
<213> ORGANISM: human

<400> SEQUENCE: 19

Leu Val Pro His Leu Gly Asp Arg Glu Lys Arg Asp Ser Val Cys Pro
1               5                   10                  15

Gln Gly Lys Tyr Ile His Pro Gln Asn Asn Ser Ile Cys Cys Thr Lys
            20                  25                  30

Cys His Lys Gly Thr Tyr Leu Tyr Asn Asp Cys Pro Gly Pro Gly Gln
        35                  40                  45

Asp Thr Asp Cys Arg Glu Cys Glu Ser Gly Ser Phe Thr Ala Ser Glu
        50                  55                  60

Asn His Leu Arg His Cys
65                  70
```

ANTI-HUTNFR1 ANTIBODY AND METHODS OF USE THEREOF FOR TREATMENT

CROSS-REFERENCE TO RELATED APPLICATIONS

This application is the U.S. national stage of International Patent Application No. PCT/EP2011/066109, filed on Sep. 16, 2011, which claims the benefit of priority under 35 U.S.C. §119 from EP Patent Application No. 10177080.8, filed on Sep. 16, 2010. The disclosures of the foregoing applications are incorporated herein by reference in their entirety.

SEQUENCE LISTING

The entire content of a Sequence Listing titled "Sequence_Listing.txt," created on Mar. 12, 2013 and having a size of 19 kilobytes, which has been submitted in electronic form in connection with the present application, is hereby incorporated by reference herein in its entirety.

The invention refers to an anti-huTNFR1 antibody of the IgG1 type and pharmaceutical preparations for use as a TNF antagonist.

BACKGROUND

Tumor necrosis factor (TNF) is a pleiotropic cytokine and a central mediator of inflammation. Elevated levels of TNF are associated with various inflammatory diseases including rheumatoid arthritis, psoriasis, and Crohn's disease. Several TNF-neutralizing reagents have been approved for the treatment of these diseases, including soluble TNF receptors (etanercept) as well as anti-TNF antibodies (infliximab, adalimumab, certolizumab pegol, golimumab), and many more are under development. With over 1 million patients treated with TNF antagonists, therapeutic efficacy is well documented. However, global TNF inhibition over a prolonged period of time increases the risk of tuberculosis reactivation, serious infections and even malignancies. Consequently, medical information of all approved anti-TNF medicines includes extensive warnings and precautions.

Two TNF receptors (CD120a, TNFR1 and CD120b, TNFR2) mediate signal transduction upon binding of TNF (Locksley et al. Cell. 2001 Feb. 23; 104(4):487-501). Pro-inflammatory responses are mainly mediated by the ubiquitously expressed TNFR1. TNFR1 is activated both by the membrane-bound form of TNF (mTNF) and soluble TNF (sTNF), which is produced from mTNF by proteolytic cleavage. In contrast, TNFR2, expressed in a more restricted manner e.g. by immune cells, endothelial cells and neurons, can only be activated by mTNF. Activation of TNFR2 mainly induces anti-apoptotic signals and can lead to cell proliferation in vitro. Furthermore, TNFR2 appears to play a role in tissue homeostasis and regeneration.

Selective inhibition of TNFR1 signaling has gained increasing attention as alternative to global TNF neutralization, which affects both TNF receptors. Recently, a TNF mutein (R1antTNF) selectively neutralizing the activity of TNFR1 has been described (Shibata et al. Cytokine. 2008 November; 44(2):229-33. Epub 2008 Sep. 23). This TNF mutein, administered either as unmodified or as PEGylated protein (PEG-R1antTNF), demonstrated therapeutic efficacy in acute murine hepatitis models and a murine collagen-induced arthritis model. The beneficial effect of selectively inhibiting TNFR1 was further supported by results from a dominant-negative TNF mutein (XPro1595), which is capable of forming inactive complexes with sTNF, thus selectively inhibiting the pro-inflammatory action mediated by TNFR1 while preserving the innate immunity to infections (Olleros et al. J Infect Dis. 2009 Apr. 1; 199(7): 1053-63).

TNFR1-selective inhibition can be also achieved with TNFR1-specific antibodies. For example, a monoclonal murine antibody, H398, and antibody described in U.S. Pat. No. 5,736,138, with selectivity for human TNFR1, showed potent inhibition of TNF-mediated signal transduction and cytotoxicity (Moosmayer et al. Ther Immunol. 1995 February; 2(1):31-40).

A humanized version of H398 is described by WO2008/113515A2. Specifically a humanized antibody was produced as Fab fragment (IZI-06.1) and exhibited in vitro neutralizing activities comparable to that of the Fab fragment of the parental antibody. Importantly, the H398 antibody did not reach complete block of TNF activity, which was interpreted by the conversion from an antagonist into a partial agonist at high concentrations. This is explained by dose dependent increase in TNFR1 crosslinking, thus potentially forming ligand independent, functional TNFR1 signalling complexes. Thus, the monovalent Fab was found to be superior over the full length (divalent) antibody because of complete lack of TNFR1 crosslinking capability, thereby avoiding any intrinsic signalling potential.

Antibodies to TNFR1 were found to have an agonistic potential by inducing a response mimicking the ligand. This response suggests that signal transduction is initiated by aggregation of receptors by binding of the multivalent TNF trimers.

Espevik et al (J. Exp. Med. 1990, 171:415-426) describe the agonistic TNFR1 receptor antibody htr-9, which is a full-length antibody found to mimic TNFalpha action.

WO2010094720 describes anti-TNFR1 single domain antibodies (dAbs) and constructs comprising such single domain antibodies.

Brocks et al. (Immunotechnology 3(3) 173-184 (1997)) describe TNF receptor antagonistic mono- and bivalent scFv derivatives.

WO2008113515 describes the anti-TNFR1 antibody H398 and humanized Fab and scFv derivatives thereof.

Armour et al. (European Journal of Immunology 29(8) 2613-2624 (1999)) describe recombinant human IgG1 molecules with mutations to reduce binding to FcgammaRI.

pFUSE-Fc plasmids of InvivoGen (San Diego, Calif., USA) are provided for different applications, e.g. for therapeutic use without cell depletion activity (InvivoGen: "IgG-Fc engineering for therapeutic use" 2007, p. 1-2, XP002616317)

Divalent anti-TNFR1 antibodies were known to bear the risk of pro-inflammatory reactions, including cytotoxicity and apoptosis, which would be contraproductive in treating TNF mediated disease conditions. Monovalent antibody fragments, like scFv, dAb or Fab typically have a short half-life and are therefore of limited use as a pharmaceutical. It was thus the objective to provide an improved anti-TNFR1 agent which would have a prolonged half-life, but avoiding any side effects caused by a TNF agonistic activity.

The object is solved by the subject matter as claimed.

SUMMARY OF THE INVENTION

According to the invention there is provided an anti-huTNFR1 antibody of the IgG1 type, which has a modified Fc region deficient in mediating effector function. In particular, the antibody according to the invention is an IgG1 antibody suitable for therapeutic use, e.g. a full-length human or humanised IgG1 antibody.

Specifically the antibody has an Fc region which comprises a mutation to downmodulate the effector function.

Preferably this is effected by glycoengineering the Fc region to downmodulate the effector function.

According to a preferred embodiment the antibody has an Fc region which is mutated to downmodulate the effector function. Preferably the Fc region comprises a heavy chain with at least one mutation selected from the group consisting of E233P, L234V, L235A, ΔG236, A327G, A330S and P331S (Kabat EU index numbering).

Preferably at least two of said mutations, more preferably at least three, four, five or all of the six mutations are engineered into the human IgG1 Fc sequence.

Preferably the antibody according to the invention is specifically binding to an epitope comprising the membrane-distal CRD1 and subdomain A1 of CRD2 of huTNFR1.

The specifically preferred binding epitope is represented by amino acid 1 to 70 in the N-terminal region of huTNFR1.

According to a preferred embodiment the antibody is binding specifically to the epitope recognized by the H398 antibody.

Preferably the antibody is binding specifically to huTNFR1 by at least two binding sites. In particular, the antibody is at least bivalent (i.e. binding to the same antigen or epitope by two valencies) or bispecific (binding to two different antigens or epitopes).

Specifically the antibody is a humanized H398 antibody.

According to one aspect a pharmaceutical preparation is provided comprising the antibody according to the invention and a pharmaceutically acceptable carrier.

According to another aspect there is provided a method of producing an antibody according to the invention employing a recombinant mammalian expression system.

Preferably the expression system employs a CHO production cell line. According to a specific aspect there is provided an anti-huTNFR1 antibody of the IgG1 type for use as a TNF antagonist without forming an agonistic TNFR1 signalling complex, as an alternative to treatment with an anti-TNF therapeutic. Such TNF antagonists, also considered as biological TNF antagonists, are typically provided for therapeutic use where the biological relevance of TNF function in the pathogenesis of chronic noninfectious inflammation of joints, skin and gut has proven.

The preferred use is for second line treatment where other anti-TNF or non biologic DMARD (disease modifying anti-rheumatic drugs) therapeutics failed.

Specifically the antibody is provided for use in treating autoimmune diseases, rheumatoid arthritis, psoriasis, psoriatic arthritis, juvenile arthritis, ankylosing spondylitis, Crohn's disease, multiple sclerosis, congestive heart failure, metabolic disease, cytokine release syndrome, septic shock, acute and chronic neurodegenerative disease, including stroke, Alzheimer and Parkinson disease, or cancer.

FIGURES

FIGS. 1a-1c: Characterization of ATROSAB. a) SDS-PAGE analysis of purified ATROSAB (4 μg/lane, Coomassie staining) analyzed under non-reducing (1) or reducing (2) conditions. b) Size exclusion chromatography of ATROSAB (the position of standard proteins is indicated). c) ELISA of ATROSAB and H398 for binding to human TNFR1-Fc.

Figure 2:
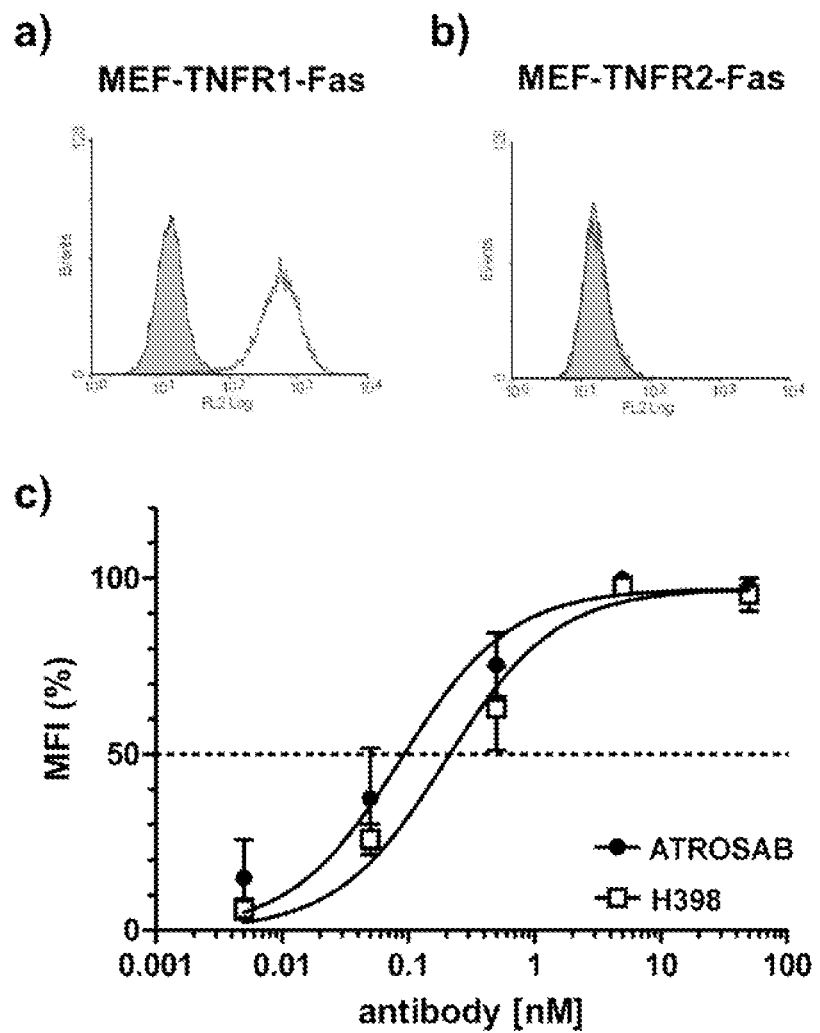

FIGS. 2a-2c: Flow cytometry analysis of binding of ATROSAB to mouse embryonic fibroblasts (MEF) transfected with human TNFR1-Fas (a) or human TNFR2-Fas (b). c) Titration of binding of ATROSAB and H398 to MEF-TNFR1-Fas (n=3).

Figure 3:
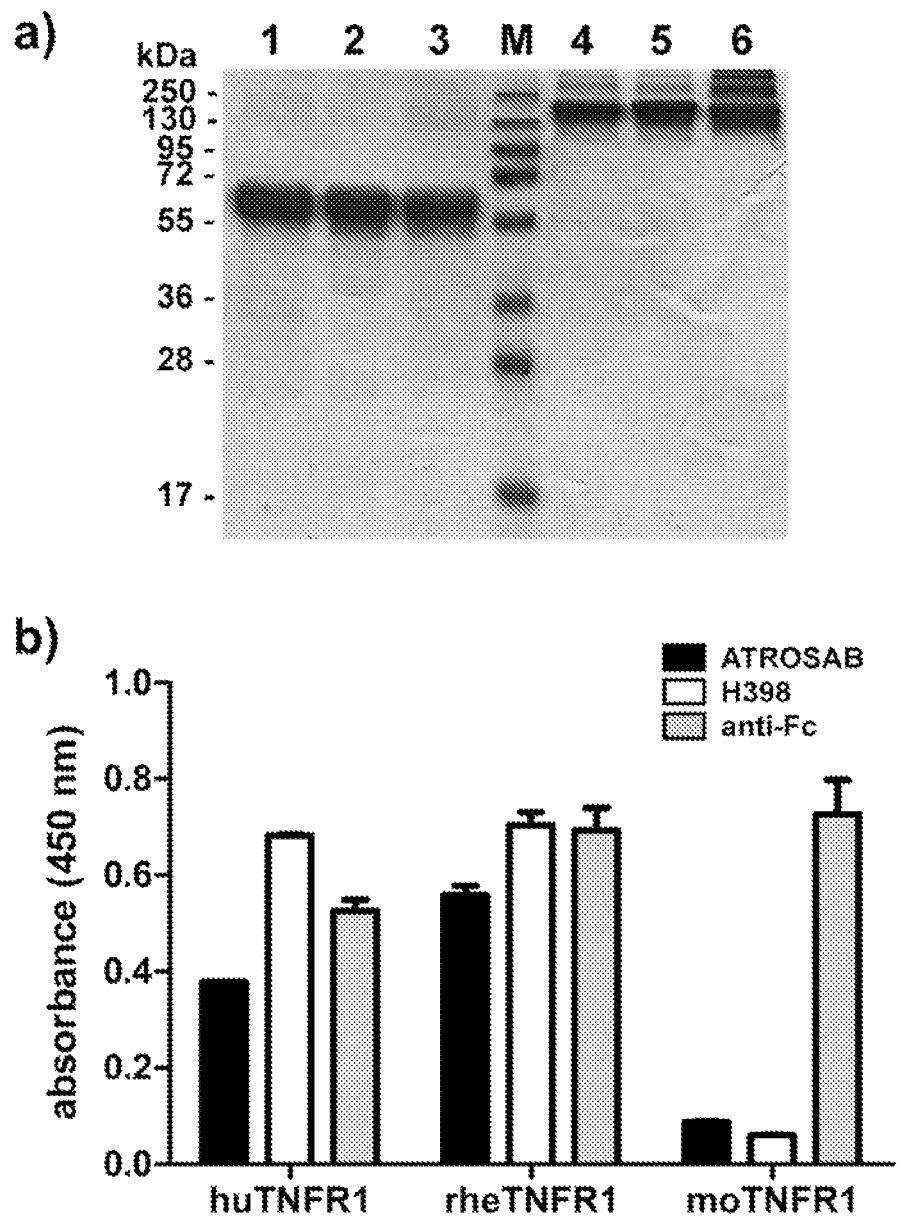

FIGS. 3a-3b: a) SDS-PAGE analysis of purified human TNFR1-Fc (1,4), mouse TNFR1-Fc (2, 5) and rhesus TNFR1-Fc (3, 6) (4 μg/lane, Coomassie staining) analyzed under reducing (1-3) and non-reducing (4-6) conditions. b) ELISA of binding of ATROSAB and H398 (5 μg/ml) to purified human TNFR1-Fc, rhesus TNFR1-Fc and mouse TNFR1-Fc. (100 ng/well). Binding was detected by HRP-conjugated anti-molgG (Fc-specific) antibody or anti-human Fab antibody, respectively. Binding of an antihuman Fc antibody (anti-Fc) was included as coating control.

FIGS. 4a-4d: Determination of affinity of H398 and ATROSAB for binding to human and rhesus TNFR1-Fc by quartz crystal microbalance (OCM) measurements. a) Binding of H398 to human TNFR1-Fc, b) binding of ATROSAB to human TNFR1-Fc, c) binding of H398 to rhesus TNFR1-Fc, and d) binding of ATROSAB to rhesus TNFR1-Fc.

Figure 5:
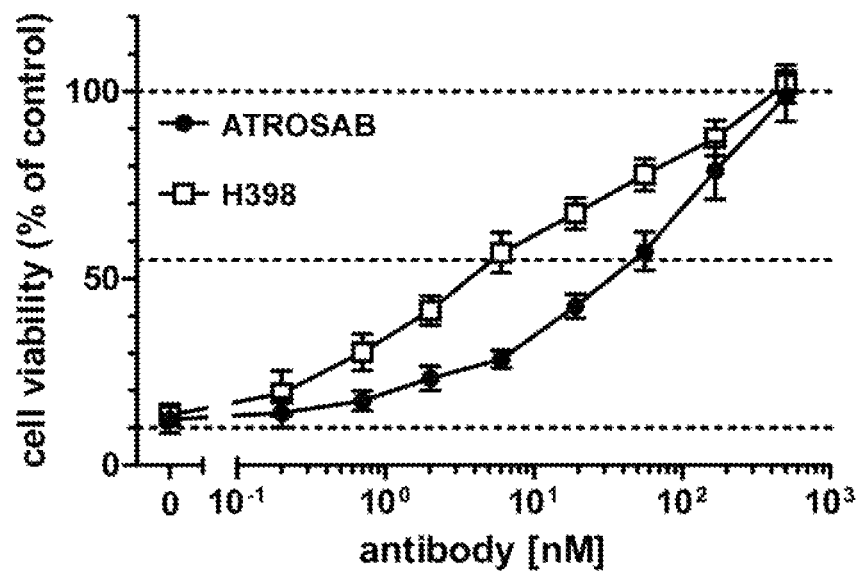

FIG. 5: Inhibition of TNF-mediated cytotoxicity (1.25 ng/ml TNF) on Kym-1 cells by ATROSAB and H398. Cells were analyzed after 6 h by crystal violet staining (n 15=3). Maximum (10% viability of control) and half maximum (55% viability of control) are displayed in dotted lines.

FIGS. 6a-6d: Inhibition of IL-6 and IL-8 secretion induced by TNF by ATROSAB and H398. HeLa cells (a) or HT1080 cells (b) were incubated with TNF (1 ng/ml) and increasing concentrations of ATROSAB or H398 and cytokine secretion were determined by ELISA (n=3). Human IgG (hulgG) was included as negative control. In the same way, effects of antibodies on cytokine secretion in the absence of TNF were determined. Compared with TNF, both antibodies had only marginal effects on IL-6 (c) and IL-8 (d) secretion.

Figure 7:
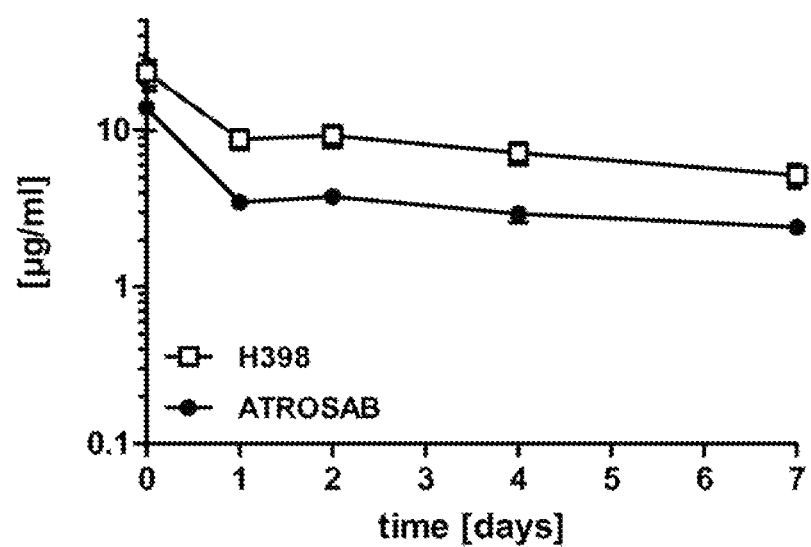

FIG. 7: Plasma half-lives of ATROSAB and H398 after a single dose i.v. injection (25 μg) into CD1 mice. Serum concentrations of antibodies were determined by ELISA.

FIGS. 8a-8b: a) Epitope mapping of ATROSAB and H398 using wild-type and chimeric human/mouse TNFR1-Fc fusion proteins. Antibodies (0.1 nM) were analyzed by ELISA for binding to the TNFR1-Fc fusion proteins. His-tagged human TNF (huTNF) was included as control. b) Sequence comparison of the identified epitope region (aa 1-70, SEQ ID NO: 19) of human (huTNFR1), mouse (moTNFR1), and rhesus (rhTNFR1) TNFR1. Cysteine residues are marked with grey boxes and the 2 positions (P23, Q24) analyzed by site-directed mutagenesis are marked by asterisks.

FIGS. 9a-9i: Sequence information of ATROSAB: a) heavy chain (SEQ ID NO: 10), b) VH (SEQ ID NO: 11), c) CH1 (SEQ ID NO: 12), d) hinge (SEQ ID NO: 13), e) CH2 (SEQ ID NO: 14), f) CH3 (SEQ ID NO: 15), g) light chain (SEQ ID NO: 16), h) VL (SEQ ID NO: 17), i) CL (SEQ ID NO: 18).

FIG. 10: Sequence information SEQ ID: 1-8.

Figure 11:
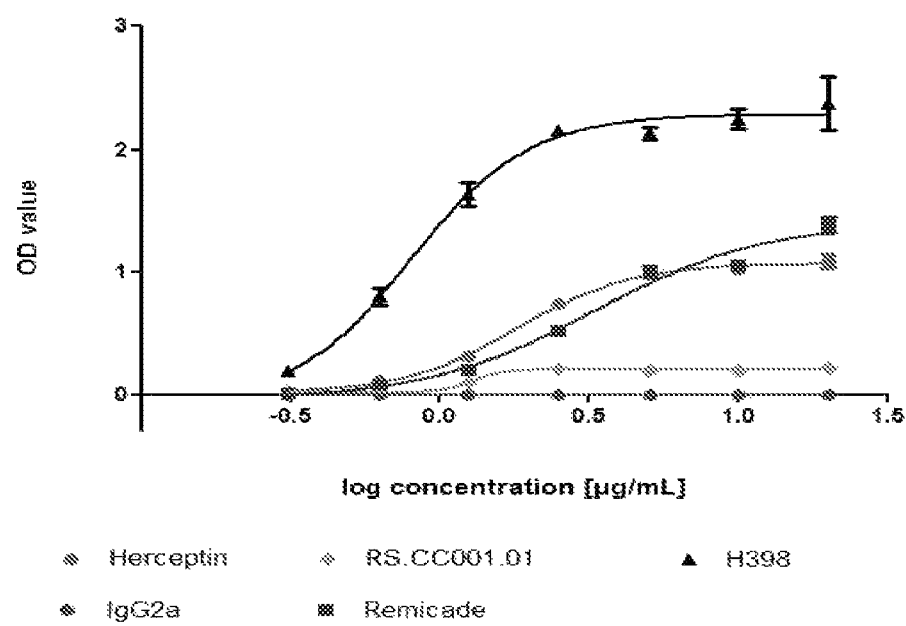

FIG. 11: Reduced CDC activity of ATROSAB: C1q binding assay for determining CDC activity. Concentration range of target antibody: 0.31 μg/ml-20 μg/ml (1:2 dilution); Concentration of C1q: 5 μg/ml); Concentration of secondary antibody: 10 μg/ml. reference antibody: Herceptin (trastuzumab, Roche), Remicade (infliximab, Centocor, Inc.), H398 (U.S. Pat. No. 5,736,138); unspecific IgG2a (negative control).

DETAILED DESCRIPTION OF THE INVENTION

According to the invention an antibody targeting human TNFR1 with no cross-reactivity to bind TNFR2 was produced. Selective inhibition of TNFR1 provides the opportunity to neutralize the pro-inflammatory activity or inflammatory responses of TNF while maintaining the advantageous immunological responses mediated by TNFR2. Specifically a full-length humanised IgG1 antibody targeting hu-TNFR1 was prepared (called herein ATROSAB). In order to avoid Fc-mediated effector functions and respective cytotoxicity, an ADCC and CDC-deficient heavy chain was used. Thus, undesired side effects, such as inhibition of TNF binding to TNFR2 or Fc mediated cytotoxicity can be avoided by the antibody according to the invention.

ATROSAB was produced in mammalian cells and showed a similar binding and neutralizing behavior as the parental mouse H398 IgG. Surprisingly however, there was no agonistic activity that would have been expected with such a full-length antibody.

Anti-TNFR1 antibodies, particularly htf-9 antibody were heretofore described to have agonistic activity activating the TNFR1 signal function due to the divalent binding and the cross-linking potential. It was therefore not expected that any anti-huTNFR1 antibody of the IgG1 type with downmodulated Fc effector functions would not show such agonistic activity. In contrast to previous assumptions, H398 antibody turned out to lack such undesired TNFR1 agonistic activity. The antibody of the invention thus can surprisingly be used as a TNF antagonist without side effects, such as those induced by activating the TNFR1 signal transduction or cytotoxicity mediated by immune effector cells directed via Fc receptor towards the Fc portion of the antibody molecule.

The term "antibody of the IgG1 type" as used herein shall refer to any kind of antibody which can bind to an antigen, including natural antibodies, mutated antibodies and (semi)-synthetic antibodies, as long as the antibody includes an IgG1 Fc region.

The term shall specifically refer to an antibody of an IgG1 type having the structure determined by a heavy chain specifically comprising the IgG1 Fc region, preferably a human Fc fragment, respective variants and derivatives thereof. Specific embodiments refer to the full-length IgG1 antibody or combinations of antibody domains which include the IgG1 Fc region. Among the specific constructs, any antibody variable domains with antigen-binding function may be combined with an Fc region, like domains of the heavy and light chains of the variable region (such as dAb, Fd, Vλ, Vκ, VH, VHH) combined with antibody constant domains, including the Fc region.

IgG antibodies are large molecules of about 150 kDa composed of 4 peptide chains. The antibodies contain two heavy chains of about 50 kDa and two light chains of about 25 kDa, thus display a tetrameric quaternary structure. The two heavy chains are linked to each other and to a light chain each by disulfide bonds. The resulting tetramer has two halves which together form the Y-like shape. Each end of the fork contains an antigen binding site. Antibodies of the invention may be engineered for bi- or multi-specific, or bi- or multivalent binding, preferably at least two or more, e.g. at least three or four specific binding sites for epitopes of antigens are obtained in the antibody according to the invention. The preferred divalent antibody according to the invention binds to TNFR1 by two binding sites, preferably formed by the antibody variable domains VH/VL.

The term "Fc region" as used according to the invention refers to the tail region of an antibody that typically interacts with cell surface receptors called Fc receptors and some proteins of the complement system. This property allows antibodies to activate the immune system. In IgG1 the Fc region is composed of two identical protein fragments, derived from the second (CH2) and third (CH3) constant domains of the antibody's two heavy chains. The Fc regions of IgGs bear a highly conserved N-glycosylation site. The N-glycans attached to this site are predominantly core-fucosylated diantennary structures of the complex type. Additionally, small amounts of these N-glycans also bear bisecting GlcNAc and α-2,6 linked sialic acids residues.

Though the antibody according to the invention could be provided as a rodent antibody, such as murine antibody, it is preferred to provide a human or humanized antibody, including chimeric antibodies, for use in human patients.

There is no limitation as to the technique of humanization of the antibody, as long as the antibody binds to the desired antigen. Examples of humanization include, without limitation thereto, complementarity determining region grafting (CDR grafting) (Jones et al. 1986, Nature 321, 522-525), specificity determining residue grafting (SDR grafting) (Kashmiri et al., 2005, Methods 36, 25-34), resurfacing of variable domains (Roguska et al., 1994, Proc. Natl. Acad. Sci. USA 91, 969-973), structure-based selection and humanization by CDR grafting (Hwang et al., 2005, Methods 36, 35-42), and de-Immunization strategies (Hellendom et al., 2004, Cancer Cell International 4 (Sppl. I), 20).

The expression "humanized antibody" used herein means any antibody in which protein engineering is used to reduce the amount of foreign ("non-human") protein sequence by swapping e.g. rodent antibody constant regions and/or variable-domain frameworks or framework residues with sequences that are found in human antibodies.

In a specific embodiment of the present invention, the antibody according to the present invention is a humanized antibody, which contains amino acid sequences of human origin and such of non-human, e.g. rodent origin.

In a preferred embodiment, the antibody of the invention or Fc region is derived from a humanized antibody obtainable by e.g. recombinant nucleic acid technology. In this regard the antibody, or at least one fragment thereof, may contain one or more mutations or variations, such as added, deleted or substituted amino acids or nucleic acids, as long as it has no negative effect on the interaction with huTNFR1. Further, the antibody may contain one or more mutations or variations, such as added, deleted or substituted amino acids or nucleic acids, which have a positive effect on the interaction of huTNFR1 and which improve the antagonistic activity of said molecule. In particular, such mutated variants have a better affinity and/or a better inhibitory activity.

For example, the antibody may be a humanized antibody having the same binding specificity as the murine antibody H398, and is preferably derived from such a parental antibody. Though the binding specificity is preferably the same, the fine specificity may change due to humanization or other mutation techniques.

According to an example the mouse anti-human TNFR1 monoclonal antibody H398 exhibiting TNFR1-neutralizing activity was humanized. This humanized antibody has been converted into an IgG1 molecule (ATROSAB) containing a modified Fc region deficient in mediating effector functions. Purified ATROSAB, produced in CHO cells, showed strong binding to human and rhesus TNFR1-Fc fusion protein and mouse embryonic fibroblasts transfected with a recombinant TNFR1 fusion protein with an affinity identical to the parental mouse antibody H398. Using chimeric human/mouse TNFR1 molecules, the epitope of ATROSAB was mapped to the N-terminal region (amino acid residues 1-70) comprising the first cysteine-rich domain (CRD1) and the A1 sub-domain of CRD2. In vitro, ATROSAB effectively inhibited typical TNF-mediated responses like apoptosis induction and activation of NFκB-dependent gene expression such as IL-6 and IL-8 production. It was further shown that ATROSAB does not mimic TNF binding to TNFR1 and thus does not trigger the undesired cytokine expression and release by HeLa or HT1080 cells in the absence of TNF. Moreover, on human peripheral blood T-cells and granulocytes no agonistic activity of ATROSAB could be discerned in the TNF-dependent cellular response models of T cell activation and oxygen production, respectively.

It turned out that the most preferred antibody of the present invention bound to the epitope that comprises or consists essentially of at least the membrane-distal CRD1 and subdomain A1 of CDR2 of huTNFR1.

In a specific embodiment the huTNFR1-antibody according to the invention comprises one or more of the complementary determining regions (CDRs) of H398, such as described in WO2008/113515, e.g. selected from the group consisting of SEQ ID NOs: 1 to 6, or parts thereof, conferring binding to huTNFR1. The CDRs of SEQ ID NOs: 1 to 6 may be present in any combination, for example two, three, four, five or six of said CDRs may be present. Additionally, multiple copies or genetic variants of any of the CDRs may be present in the huTNFR1-antibody of the present invention, as long as the antibody shows sufficient affinity towards human TNFR1.

According to a specific embodiment the huTNFR1-antibody of the present invention comprises the amino acid sequence according to SEQ ID NO.: 7 as variable domain of the heavy chain (VH) and the amino acid sequence according to SEQ ID NO.: 8 as variable domain of the light chain (VL).

The sequences SEQ ID NO 1-8 are as follows:

There is not a specific limitation with respect to the tag usable in the present invention, as far as it has no or tolerable negative impact on the binding of the huTNFR1-antibody to huTNFR1 or the immunogenic response when administered to a human being. Examples of suitable tags include His-tag, Myc-tag, FLAG-tag, Strep-tag, Calmodulin-tag, GST-tag, MBP-tag, and S-tag.

A "derivative" of an antibody or Fc molecule is herein understood as any combination with one or more peptides, polypeptides or protein domains, such as antibody domains and/or a fusion protein in which any domain of the antibody of the invention may be bound or fused at any position with one or more other proteins (such as other antibodies or antibody domains, ligands, enzymes, toxins and the like). A derivative of the antibody of the invention may also be obtained by association or binding to other substances by various chemical techniques such as covalent coupling, electrostatic interaction, disulphide bonding etc. Other substances bound to the antibody may be lipids, carbohydrates, nucleic acids, organic and inorganic molecules or any combination thereof (e.g. PEG, prodrugs or drugs). A derivative would also comprise an antibody with the homologous amino acid sequence, which may contain non-natural or chemically modified amino acids. Further derivatives are provided as antibody fragments or variants.

```
SEQ ID NO 1: CDR1
Gly Tyr Thr Phe Thr Asp Phe Tyr Ile Asn

SEQ ID NO 2: CDR2
Trp Ile Gly Glu Ile Tyr Pro Tyr Ser Gly His Ala Tyr Tyr Asn Glu Lys Phe Lys Ala

SEQ ID NO 3: CDR3
Trp Asp Phe Leu Asp Tyr

SEQ ID NO 4: CDR4
Arg Ser Ser Gln Ser Leu Leu His Ser Asn Gly Asn Thr Tyr Leu His Trp Tyr

SEQ ID NO 5: CDR5
Leu Leu Ile Tyr Thr Val Ser Asn Arg Phe Ser

SEQ ID NO 6: CDR6
Ser Gln Ser Thr His Val Pro Tyr Thr

SEQ ID NO 7: VH
Gln Val Gln Leu Val Gln Ser Gly Ala Glu Val Lys Lys Pro Gly Ser Ser Val Lys

Val Ser Cys Lys Ala Ser Gly Tyr Thr Phe Thr Asp Phe Tyr Ile Asn Trp Val Arg Gln Ala

Pro Gly Gln Gly Leu Glu Trp Ile Gly Glu Ile Tyr Pro Tyr Ser Gly His Ala Tyr Tyr Asn Glu

Lys Phe Lys Ala Arg Val Thr Ile Thr Ala Asp Lys Ser Thr Ser Thr Ala Tyr Met Glu Leu

Ser Ser Leu Arg Ser Glu Asp Thr Ala Val Tyr Tyr Cys Ala Arg Trp Asp Phe Leu Asp

Tyr Trp Gly Gln Gly Thr Thr Val Thr Val Ser Ser

SEQ ID NO 8: VL
Asp Ile Val Met Thr Gln Ser Pro Leu Ser Leu Pro Val Thr Pro Gly Glu Pro Ala

Ser Ile Ser Cys Arg Ser Ser Gln Ser Leu Leu His Ser Asn Gly Asn Thr Tyr Leu His Trp

Tyr Leu Gln Lys Pro Gly Gln Ser Pro Gln Leu Leu Ile Tyr Thr Val Ser Asn Arg Phe Ser

Gly Val Pro Asp Arg Phe Ser Gly Ser Gly Ser Gly Thr Asp Phe Thr Leu Lys Ile Ser Arg

Val Glu Ala Glu Asp Val Gly Val Tyr Tyr Cys Ser Gln Ser Thr His Val Pro Tyr Thr Phe

Gly Gly Gly Thr Lys Val Glu Ile Lys Arg
```

In yet another embodiment of the present invention, the huTNFR1-antibody comprises an additional tag allowing specific interaction with a biologically acceptable compound.

The term "antibody fragment" as used herein means any portion of an antibody as defined above as long as it has the ability to bind to the desired antigen (huTNFR1) binding sites. Moreover, a fragment of the antibody according to the present invention comprises several different portions from said antibody, in any case an Fc region.

The term "variants" shall refer to mutants, e.g. obtained by site-directed mutagenesis methods, in particular to delete, exchange or introduce inserts into a specific antibody region, preferably into the constant domains to engineer the antibody effector function or half-life, or in the variable domains to improve antigen-binding properties, e.g. by affinity maturation techniques. Any of the known mutagenesis methods may be employed, including point mutations at desired positions, e.g. obtained by randomisation techniques. In some cases positions are chosen randomly, e.g. with either any of the possible amino acids or a selection of preferred amino acids to randomise the antibody sequences. The term "variant" specifically shall refer to functionally active variants.

The term "functionally active variant" of a molecule, such as the antibody as used herein, means a sequence resulting from modification of this sequence by insertion, deletion or substitution of one or more amino acids or nucleotides within the sequence or at either or both of the distal ends of the sequence, and which modification does not affect (in particular impair) the activity of this sequence. In the case of a binding site having specificity to a selected target antigen, the functionally active variant of a molecule would still have the predetermined binding specificity, though this could be changed, e.g. to change the fine specificity to a specific epitope, the affinity, the avidity, the Kon or Koff rate, etc. In a preferred embodiment the functionally active variant a) is a biologically active fragment of the molecule, the fragment comprising at least 50% of the sequence of the molecule, preferably at least 70%, more preferably at least 80%, still more preferably at least 90%, even more preferably at least 95% and most preferably at least 97%, 98% or 99%; b) is derived from the molecule by at least one amino acid substitution, addition and/or deletion, wherein the functionally active variant has a sequence identity to the molecule or part of it, such as an antibody of at least 50% sequence identity, preferably at least 60%, more preferably at least 70%, more preferably at least 80%, still more preferably at least 90%, even more preferably at least 95% and most preferably at least 97%, 98% or 99%; and/or c) consists of the molecule or a functionally active variant thereof and additionally at least one amino acid or nucleotide heterologous to the polypeptide or the nucleotide sequence, preferably wherein the functionally active Fc variant is derived from any of the naturally occurring variants of human IgG Fc (SEQ ID No:9):

TCPPCPAPELLGGPSVFLFPPKPKDTLMISRTPEVTCVVVDVSHEDPEV

KFNWYVDGVEVHNAKTKPREEQYNSTYRVVSVLTVLHQDWLNGKEYKCK

VSNKALPAPIEKTISKAKGQPREPQVYTLPPSRDELTKNQVSLTCLVKG

FYPSDIAVEWESNGQPENNYKTTPPVLDSDGSFFLYSKLTVDKSRWQQG

NVFSCSVMHEALHNHYTQKSLSLSPGK

Functionally active Fc variants may be obtained by changing the sequence above and are characterized by having a biological activity similar to that displayed by the respective sequence, including the ability to stabilize an antibody or to confer a prolonged half-life. The preferred Fc variants as used in an antibody according to the invention comprise mutations to reduce the Fc effector function.

Functionally active variants may be obtained by sequence alterations in the polypeptide or the nucleotide sequence, wherein the sequence alterations retains a function of the unaltered polypeptide or the nucleotide sequence, when used in combination of the invention. Such sequence alterations can include, but are not limited to, (conservative) substitutions, additions, deletions, mutations and insertions.

In one preferred embodiment of the invention, the functionally active variant of the antibody according to the invention is essentially identical to the variant described above, but differs from its polypeptide or the nucleotide sequence, respectively, in that it is derived from a homologous sequence of a different species. These are referred to as naturally occurring variants.

The term "functionally active variant" also includes naturally occurring allelic variants, as well as mutants or any other non-naturally occurring variants. As is known in the art, an allelic variant is an alternate form of a (poly) peptide that is characterized as having a substitution, deletion, or addition of one or more amino acids that does essentially not alter the biological function of the polypeptide.

Conservative substitutions are those that take place within a family of amino acids that are related in their side chains and chemical properties. Examples of such families are amino acids with basic side chains, with acidic side chains, with non-polar aliphatic side chains, with non-polar aromatic side chains, with uncharged polar side chains, with small side chains, with large side chains etc.

"Percent (%) amino acid sequence identity" with respect to the polypeptide sequences identified herein is defined as the percentage of amino acid residues in a candidate sequence that are identical with the amino acid residues in the specific polypeptide sequence, after aligning the sequence and introducing gaps, if necessary, to achieve the maximum percent sequence identity, and not considering any conservative substitutions as part of the sequence identity. Those skilled in the art can determine appropriate parameters for measuring alignment, including any algorithms needed to achieve maximal alignment over the full length of the sequences being compared.

As used herein, the term "specifically binds" or "specific binding" refers to a binding reaction which is determinative of the cognate ligand of interest in a heterogeneous population of molecules. Thus, under designated conditions (e.g. immunoassay conditions), the antibody according to the invention binds to its particular target and does not bind in a significant amount to other molecules present in a sample. The specific binding means that binding is selective in terms of target identity, high, medium or low binding affinity or avidity, as selected. Selective or specific binding is usually achieved if the binding constant or binding dynamics is at least 10 fold different, preferably the difference is at least 100 fold, and more preferred a least 1000 fold.

The term "antibody" or "Fc region" shall specifically include those mutants or functionally active variants with deficient Fc receptor-binding properties, e.g. glycoengineered Fc regions or those with downmodulated effector function and/or prolonged half-life.

The term "effector function" as used for the purpose of the invention shall mean the effect mediated by an effector ligand binding to the Fc region of an antibody. Exemplary effector ligands are Fc receptors or Fc receptor-like molecules binding to immunoglobulins. An Fc receptor is a protein found on the surface of certain cells—including natural killer cells, macrophages, neutrophils, and mast cells—that contribute to the protective functions of the immune system. There are several different types of Fc receptors, which are classified based on the type of antibody that they recognize; those that bind the most common class of antibody, IgG, are called Fc-gamma receptors (FcγR or FcgR). The family of FcγRs includes several members: FcγRI (CD64), FcγRIIA (CD32a), FcγRIIB (CD32b), FcγRIIIA (CD16a), FcγRIIIB (CD16b). Among the effector molecules there are also complement proteins, such as C1q.

Another Fc receptor, the neonatal Fc receptor (FcRn) also binds IgG and is involved in preservation and half-life of this antibody. According to the invention it is preferred that the function mediated by FcRn is not downmodulated.

The term "downmodulate" shall refer to the reduction of an effect mediated by a gene or a group of genes, or a polypeptide, by gene mutation or downregulation of the gene expression or activity of gene expression products, such as nucleic acids or polypeptides, specifically by reduction of binding properties, like affinity, avidity or specificity, including inhibition of binding a ligand, such as an effector ligand, at least in part. Thereby an antibody exhibiting a reduced ADCC and/or CDC can be obtained.

Antibody-dependent cell-mediated cytotoxicity (ADCC), is the killing of antibody-coated target cells by cells with Fc receptors that recognize the constant region of the bound antibody. Most ADCC is mediated by NK cells that have the Fc receptor FcgRIII or CD16 on their surface. Typical assays employ target cells, like Ramos cells, incubated with serially diluted antibody prior to the addition of freshly isolated effector cells. The ADCC assay is then further incubated for several hours and % cytotoxicity detected. Usually the Target: Effector ratio is about 1:16, but may be 1:1 up to 1:50.

Complement-dependent cytotoxicity (CDC) is a mechanism of killing cells in which antibody bound to the target cell surface fixes complement, which results in assembly of the membrane attack complex that punches holes in the target cell membrane resulting in subsequent cell lysis. The commonly used CDC assay follows the same procedure as for ADCC determination, however, with complement containing serum instead of effector cells.

The antibody according to the invention has an Fc region deficient in mediating effector functions, preferably a downmodulated cytotoxic activity as determined by either of ADCC and CDC assay, preferably in a way to provide a significant decrease in the percentage of cytolysis as compared to a control. The absolute percentage decrease preferably is higher than 10%, more preferably higher than 20%, even more preferred higher than 30%, 40%, 50%, 60%, 70%, 80%, 90%. Most preferred the antibody is essentially free of at least one of ADCC or CDC activity, e.g. having less than 10% of the typical ADCC and/or CDC activity as compared to a native (unmodified) antibody. The term "essentially free" as used herein shall also refer to those antibody variants that are completely lacking such an activity as measured in a standard assay.

Specific point mutations within the Fc region are well-known in the art to effectively downmodulate the effector function. Specifically preferred mutations are employed in the region of the binding site on human IgG for the different Fcgamma receptors (FcgR), which would provide for abrogating immune recruitment via FcgR. The binding site on human and murine IgG for FcgR was mapped primarily to the lower hinge region composed of IgG residues 233-239. Additional broad segments, e.g. Gly316-Lys338 were determined for human FcγRI, Lys274-Arg301 and Tyr407-Arg416 for human FcγRIII. The 3.2-Å crystal structure of the human IgG1 Fc fragment with human FcγRIIIA delineated IgG1 residues Leu234-Ser239, Asp265-Glu269, Asn297-Thr299, and Ala327-Ile332 as involved in binding to FcγRIIIA. A review referring to high resolution mapping of human IgG1 for human FcγR receptors (FcγRI, FcγRIIA, FcγRIIB, and FcγRIIIA) is provided by Shields et al (J Biol. Chem. 2001 Mar. 2; 276(9):6591-604. Epub 2000 Nov. 28).

The term "point mutations" as used herein shall refer to a single base substitution, wherein a single base nucleotide is replaced with another nucleotide of the genetic material, DNA or RNA.

All numbering of the amino acid sequences of the antibody according to the invention is according to the Kabat EU index.

The Fc region as used according to the invention may be glycosylated or not, depending on specific mutations or the choice of expression system.

The term "glycoengineered" with respect to antibody sequences or Fc region shall refer to glycosylation variants having modified ADCC and/or CDC as a result of the glycoengineering. All antibodies contain carbohydrate structures at conserved positions in the heavy chain constant regions, with each isotype possessing a distinct array of N-linked carbohydrate structures, which variably affect protein assembly, secretion or functional activity. IgG1 type antibodies are glycoproteins that have a conserved N linked glycosylation site at Asn297 in each CH2 domain. The two complex bi-antennary oligosaccharides attached to Asn297 are buried between the CH2 domains, forming extensive contacts with the polypeptide backbone, and their presence is essential for the antibody to mediate effector functions such as antibody dependent cellular cytotoxicity (ADCC) (Lifely, M. R., et al., Glycobiology 5: 813-822 (1995). Removal of N-Glycan at N297, eg through mutating N297, e.g. to A, or T299 typically results in aglycosylated Fc with reduced ADCC.

Major differences in antibody glycosylation occur between cell lines, and even minor differences are seen for a given cell line grown under different culture conditions. Expression in bacterial cells typically provides for an aglycosylated antibody that is essentially free of ADCC and/or CDC activity.

The antibody according to the invention is preferably conjugated to a label or reporter molecule, e.g. selected from the group consisting of organic molecules, enzyme labels, radioactive labels, colored labels, fluorescent labels, chromogenic labels, luminescent labels, haptens, digoxigenin, biotin, metal complexes, metals, colloidal gold and mixtures thereof. Antibodies conjugated to labels or reporter molecules may be used, for instance, in assay systems or diagnostic methods.

The antibody according to the invention may be conjugated to other molecules which allow the simple detection of said conjugate in, for instance, binding assays (e.g. ELISA) and binding studies.

Methods for producing and characterizing an antibody according to the invention are well-known in the art. In a preferred embodiment, antibody variants are produced and screened for predefined properties using one or more cell-based assays employing huTNFR1 expressing cells or in vivo assays. For such assays, the antibody is typically added exogenously such that cells can be bound, e.g. in the presence and absence of TNFalpha to determine the antagonistic and agonistic activity. These assays are typically based on the function of the immunoglobulin; that is, the ability of the antibody to bind to huTNFR1 and mediate some biochemical event, for example the blocking of TNFalpha binding to said cells, e.g. in a competitive binding assay, TNF/receptor binding inhibition, the reduction of cytokine expression in the presence or absence of TNF, specifically inflammatory interleukins, such as IL6 or IL8, apoptosis, and the like.

Such assays often involve monitoring the response of cells to the antibody, for example cell survival, cell death, change in cellular morphology, or transcriptional activation such as cellular expression of a natural gene or reporter gene. For some assays additional cells or components, that is in addition to the target cells, may need to be added, for example serum complement, or effector cells such as peripheral blood monocytes (PBMCs), NK cells, macrophages, and the like. Such additional cells may be from any organism, preferably humans, mice, rat, rabbit, and monkey.

Methods for monitoring cell death or viability are known in the art, and include the use of dyes, immunochemical, cytochemical, and radioactive reagents. For example, caspase staining assays may enable apoptosis to be measured, and uptake or release of radioactive substrates or fluorescent dyes such as alamar blue may enable cell growth or activation to be monitored.

Transcriptional activation may also serve as a method for assaying function in cell-based assays. In this case, response may be monitored by assaying for natural genes or immunoglobulins which may be upregulated, for example the release of certain interleukins may be measured, or alternatively the readout may be via a reporter construct. Cell-based assays may also involve the measure of morphological changes of cells as a response to the presence of an antibody according to the invention.

The antibody of the present invention preferably has a TNF antagonistic activity, reducing the inflammatory reaction caused by an increased TNFalpha level in the circulation that could result in undesired inflammatory responses, apoptosis and necrosis. The preferred antibody has an antagonistic activity corresponding to an $IC_{50}$ of less than 100 nM, preferably less than 20 nM, more preferred less than 10 nM, most preferred in the single digit nanomolar range or less, as measured in a cell-based assay employing TNF at a half-maximal saturation concentration, preferably in the range of 1-100 nM TNF, e.g. by a test system as further described by the examples below.

The TNF mimetic agonistic activity is preferably measured in the same cell-based assay, however, without employing TNF, e.g. by a test system as further described by the examples below. The antibody of the invention preferably has no significant agonistic activity, if the incubation of HeLa or HT1080 cells in the absence of TNF results in only marginal induction of cytokine, e.g. elevated IL6 or IL8 levels of less than 0.5 ng/ml at concentrations of at least 5 nM or around 10 nM. Preferably there was marginal or negative cytokine production, which can be determined by the amount of less than 10 pg/$10^5$ cells. In a preferred example the cytokine expression and release was less than 2.5 pg/100.000 cells in 18 h. Preferably the agonistic activity is thus less than 10% of the response of a comparable TNF concentration, preferably less than 5% of the equivalent TNF response.

It has been particularly proven that an exemplary antibody according to the invention did not trigger the expression or release of inflammatory cytokines, such as IL6 or IL8. Thereby the undesired inflammatory conditions or tissue damage can be avoided. Further undesirable cytotoxicity which would have been caused by Fc effector function is reduced to a minimum. The reduction of such side reactions is particularly useful for providing pharmaceutical preparations to treat chronic disease.

The antibody of the invention is preferably provided as a recombinant protein produced by a recombinant expression system employing a host cell, e.g. by expression in the periplasmic space of E. coli or by expression as a secreted protein in a eukaryotic expression system such as yeast or mammalian, e.g. by CHO, HEK or human production host cell lines.

The term "expression system" refers to nucleic acid molecules containing a desired coding sequence and control sequences in operable linkage, so that hosts transformed or transfected with these sequences are capable of producing the encoded proteins. In order to effect transformation, the expression system may be included on a vector; however, the relevant DNA may then also be integrated into the host chromosome. Alternatively, an expression system can be used for in vitro transcription/translation.

Chinese hamster ovary (CHO) cells have been most commonly used for antibody production. In addition to providing suitable glycosylation patterns, these cells allow consistent generation of genetically stable, highly productive clonal cell lines. They can be cultured to high densities in simple bioreactors using serum free media, and permit the development of safe and reproducible bioprocesses.

Host cells are most preferred, when being established, adapted, and completely cultivated under serum free conditions, and optionally in media which are free of any protein/peptide of animal origin.

A preferred pharmaceutical composition according to the invention comprises a therapeutically effective amount of the huTNFR1-antibody as defined above and optionally one or more additional components selected from the group consisting of a pharmaceutically acceptable carrier, pharmaceutically acceptable salts, an auxiliary agent, a stabilizer, a diluent and a solvent, or any combination thereof.

According to the invention a method of treating a patient comprises the step of administering a therapeutically effective amount of the above-defined huTNFR1-antibody to a patient in need thereof. A therapeutically effective amount typically is in the range of 0.5-500 mg, preferably 1-400 mg, even more preferred up to 300 mg, up to 200 mg, up to 100 mg or up to 10 mg, though higher doses may be indicated e.g. for treating acute disease conditions.

In one embodiment, an antibody according to the present invention is the only therapeutically active agent administered to a patient. Alternatively, the antibody according the present invention is administered in combination with one or more other therapeutic agents, including but not limited to TNFalpha antagonists, anti-inflammatory agents, cytokines, growth factors, or other therapeutic agents. The TNF antagonistic antibody may be administered concomitantly or consecutively with one or more other therapeutic regimens, preferably with anti-TNF therapeutics, such as anti-TNF antibodies. The antibody of the present invention is preferably administered to the patient as a second-line therapy where anti-TNF therapeutics were not efficient, either as acute or chronic treatment. The specifically preferred medical use is for treating chronic disease.

The preferred indications typically relate to indications of an anti-TNF therapeutic and the antibody of the present invention is used as an alternative to conventional anti-TNF therapeutics.

Specifically the pharmaceutical composition of the present invention is suitable for treating autoimmune diseases, rheumatoid arthritis, psoriasis, psoriatic arthritis, juvenile arthritis, ankylosing spondylitis, Crohn's disease (Morbus Crohn), multiple sclerosis, congestive heart failure, metabolic disease, cytokine release syndrome, septic shock, acute and chronic neurodegenerative disease, including stroke, Alzheimer and Parkinson disease. Further appropriate indications include colitis ulcerosa and other chronic inflammatory and/or autoimmune diseases, acute fulminant viral or bacterial infections, metabolic diseases, acute neurodegenerative diseases, chronic neurodegenerative diseases, genetically inherited diseases with TNF/TNFR1 as the causative pathologic mediator, preferably selected from periodic fever syndrome and Cherubism, and cancer.

Pharmaceutical compositions are contemplated wherein the antibody of the present invention and one or more therapeutically active agents are formulated. Stable formulations of the antibody of the present invention are prepared for storage by mixing said antibody having the desired degree of purity with optional pharmaceutically acceptable carriers, excipients or stabilisers, in the form of lyophilized formulations or aqueous solutions. The formulations to be used for in vivo administration are sterile. This is readily accomplished by filtration through sterile filtration membranes or other methods. The antibody and other therapeutically active agents disclosed herein may also be formulated as immunoliposomes, and/or entrapped in microcapsules.

The pharmaceutical composition comprising an antibody of the present invention, preferably in the form of a sterile aqueous solution, may be administered in a variety of ways, including, but not limited to, subcutaneously, intravenously, orally, intranasally, intraotically, transdermally, mucosal, topically (e.g., gels, salves, lotions, creams, etc.), intraperitoneally, intramuscularly, intrapulmonary, vaginally, parenterally, rectally or intraocularly.

The foregoing description will be more fully understood with reference to the following examples. Such examples are, however, merely representative of methods of practicing one or more embodiments of the present invention and should not be read as limiting the scope of invention.

Example

Materials

Horseradish peroxidase (HRP)-conjugated anti-mouse IgG (Fc specific) antibody, HRP-conjugated anti-human IgG (whole molecule, Fc specific, Fab specific) antibodies, respectively, were purchased from Sigma (Taufkirchen, Germany). PE-labeled anti-mouse (whole molecule) and anti-human IgG (γ-chain specific) antibodies, respectively, were purchased from Sigma (Taufkirchen, Germany). Mouse embryonic fibroblasts (MEF) transfected with TNFR1-Fas (MEF-TNFR1-Fas) and TNFR2-Fas (MEF-TNFR2-Fas), respectively, were grown in RPMI 1640 medium, 5% FCS, 2 mM L-glutamine, 2 µg/ml puromycin. The human rhabdomyosarcoma cell line Kym-1 was grown in RPMI 1640 medium, 10% FCS, 2 mM L-glutamine and HT1080 wt cells and HeLa cells were grown RPMI 1640 medium, 5% FCS, 2 mM L-glutamine.

Production of IZI-06.1 IgG (ATROSAB)

DNA encoding the light and heavy chain of ATROSAB including Igκ signal sequences and codon-optimized for production in CHO cells was produced synthetically employing the sequence information of WO2008/113515A2 (Geneart, Regensburg, Germany). The light chain (LC) DNA was cloned as BamHI/NotI fragment into shuttle vector pCV072 (Celonic GmbH, Julich, Germany) and the heavy chain (HC) DNA was cloned as KasI/NheI fragment into pFUSE (InvivoGen, Toulouse, France). The Fc region encoded by pFUSE was changed to reconstitute the correct preferred allotype G1m1,17 (E356D, M358L, G431A). pFUSE-HC was digested with SmiI (SwaI) and the resulting blunt end fragment containing the entire HC expression cassette was cloned into pCV072-LC digested with PsiI. In this bicistronic expression cassette, the light chain is under the control of the PhEF1-HTLV promotor and the heavy chain gene is controlled by the PCMV enhanced promotor.

The stable transfected CHO cells were grown in CDM4PermAB (Thermo Fischer, Erembodegem, Belgium) and cultivated in fed-batch mode in a 25 L wave bioreactor system (Sartorius Stedim, Melsungen, Germany) with a soy hydrolisate feeding solution (Kerry Biosciences, Almere, Netherlands). Antibody was purified from cell culture supernatant by using protein A chromatography (GE Healthcare, Uppsala, Sweden) followed by a membrane intermediate step with Sartobind Q single Sep mini (Sartorius Stedim. Melsungen, Germany) Final product was obtained via a buffer exchange step.

Production of TNFR1-Fc Fusion Proteins

DNA encoding the extracellular region of human TNFR1 (aa 29-211), rhesus TNFR1 (aa 27-209), and mouse TNFR1 (aa 30-212) was produced synthetically (Geneart, Regensburg, Germany) using the sequence information of UniProtKB (Swiss-Prot) entry P19438 (human (*Homo sapiens*) TNFR1), introducing appropriate restriction sites between the individual domains, and cloned into pSecTagL1-Fc (modified from pSecTag-FcHis, (Muller et al. J. Immunol. Methods (2008) 339(1): 90-8)). Chimeric human/mouse TNFR1-Fc fusion proteins were generated by exchanging the different regions between human and mouse TNFR1-Fc. HEK293 cells were transfected with plasmid DNA using lipofectamine (Invitrogen, Karlsruhe, Germany) and stably transfected clones were selected in the presence of zeocin as described (Muller et al. J. Biol. Chem. (2007) 282(17):12650-60). Cells were expanded in RPMI, 5% FCS, 2 mM L-glutamine to 90% confluence. For protein production, the medium was substituted with Opti-MEM I (Invitrogen, Karlsruhe Germany) and supernatant was collected every 3-4 days. Proteins were purified from cell culture supernatant by protein A chromatography. In brief, supernatants were adjusted to pH 8 by adding 1/10 volume of 1 M TrisHCl pH 8.0 and loaded onto a protein A-sepharose CL-4B column (Sigma, Taufkirchen, Germany). Bound protein was eluted with 100 mM glycine pH 3.0, neutralized by adding 1/10 volume 1 M TrisHCl pH 8.0 and protein containing fractions were dialyzed against PBS. Protein concentrations were determined photometrically and purity was analyzed by SDS-PAGE and immunoblotting using an HRP-conjugated anti IgG (Fc specific) antibody (Sigma, Taufkirchen, Germany).

Protein Characterization

Size exclusion chromatography (SEC) was performed by HPLC using a BioSuite™ 250, 5 µm HR SEC (Waters GmbH, Eschborn, Germany). The following standard proteins were used: apoferritin (443 kDa), β-amylase (200 kDa), bovine serum albumin (67 kDa), carbonic anhydrase (29 kDa), aprotinin (6.5 kDa).

Affinity Measurements

Affinities of the antibodies were determined by quartz crystal microbalance measurements (QCM; Attana A-100 C-Fast system, Stockholm, Sweden). Binding experiments were performed in PBS 0.005% Tween 20 at a flow rate of 25 to 35 µl/min and temperature was controlled at 20° C. The TNFR1-Fc fusion proteins were chemically immobilized on an Attana carboxyl sensor chip by amine coupling at a concentration of 50 µg/ml according to the manufacturer's protocol resulting in a signal increase (frequency shift) of approximately 200 Hz. Antibodies were analyzed at concentration between 62.5 and 3.9 nM (4 measurements per concentration). The chip was regenerated with 10 mM glycine-HCl, pH 3.0. Buffer injections were performed prior to each sample injection to use as a reference in Attester Evaluation. Data were collected by Attester 3.0 (Version 3.1.1.8, Attana, Stockholm, Sweden) and analyzed by ClampXP (Myszka and Morton 1998). A mass transport model (Myszka 1997) was fitted to the data.

ELISA

Recombinant human TNFR1-Fc fusion protein was immobilized in 96-well-plates (50 ng/well in PBS) overnight at 4°

C. After 2 h blocking with 2% (w/v) dry milk/PBS, recombinant antibody fragments were titrated in duplicates and incubated for 1 h at RT. Detection was performed with HRP-conjugated anti-human IgG (Fab-specific) antibody and HRP-conjugated anti-mouse IgG (Fc-specific) using TMB substrate (1 mg/ml TMB, sodium acetate buffer pH 6.0, 0.006% $H_2O_2$). The reaction was stopped with 50 µl of 1 M $H_2SO_4$. Absorbance was measured at 450 nm in an ELISA-reader.

Flow Cytometry

Binding to TNFR1-Fas or TNFR2-Fas transfected MEF cells was analyzed by flow cytometry. Cells (2×105) were incubated with dilution series of antibodies for 4 h at 4° C. Cells were then washed with PBS and bound antibodies were detected with PE-labeled goat anti-mouse or anti-human antibody. Cells were analyzed by flow cytometry (Cytomics FC 500, Beckmann-Coulter, Krefeld, Germany). Data were evaluated with the program WinMDI, version 2.9, and fitted with GraphPrism software (La Jolla, USA) from 3 independent binding curves.

Cytotoxicity

Kym-1 cells ($1.5×10^4$ cells/100 µl) were grown in 96-well plates over night. A constant amount of human soluble TNFalpha (1.25 ng/ml in medium) was applied after preincubation with antibodies in triplicates (concentrations as indicated in the figures) in medium for 1 h. After 7 h cells were stained by crystal violet (20% methanol, 0.5% crystal violet) for 15 min. The wells were washed with $H_2O$ and air-dried. The dye was resolved with methanol for 15 min and optical density at 550 nm was determined (Tecan infinite M200, Crailsheim, Germany).

IL-6 and IL-8 Assays

HT1080 cells ($2.0×10^5$ cells/100 µl) were grown in 96-well plates over night. The next day, the medium was exchanged to remove constitutively produced IL-8 and the cells were incubated in duplicates together with serial dilutions of human soluble TNF for additional 18 h. Induction of IL-8 production and secretion into the culture supernatant was determined by an IL-8-Sandwich ELISA (ImmunoTools, Friesoythe, Germany) according to the manufacturer's protocol. In addition, cells were incubated with serial dilutions of antibodies in presence of TNFalpha (constant 1 ng/ml) and analyzed for IL-8 secretion after 18 h of incubation. In the same way, we analyzed the inhibitory effects of the antibodies on TNF-mediated secretion of IL-6 from HeLa cells using an IL-6 sandwich ELISA (ImmunoTools, Friesoythe, Germany) according to the manufacturer's protocol. The agonistic activity was measured in the absence of TNF.

CDC Activity: Binding to C1q

Lack of agonistic activity of ATROSAB has also been demonstrated in the standard C1q binding assay. C1q is the first subcomponent of the C1 complex of the classical pathway of complement activation, which is also involved in cell lysis. Thus, compounds binding to C1q will lead to complement activation and subsequently to cell lysis. In the experiments performed, the immunoglobulin Herceptin (trastuzumab, Roche), which is known to induce cell lysis and is used for the treatment of metastatic breast and gastric cancer, was used as a positive control; Immunoglobulin G2a as a negative control. As shown in FIG. 11, ATROSAB does not significantly bind to C1q, which is in clear contrast to the non-selective TNF-receptor antagonist Remicade (Infliximab, Centocor, Inc.), which was used as a comparator in the study. These results confirm that Atrosab does not induce complement dependent cytotoxicity.

Results

Production and Binding Activity of IZI-06.1 IgG (ATROSAB)

The humanized anti-human TNFR1 Fab IZI-06.1 (WO2008/113515) was converted into a human IgG1 using a heavy chain with abolished effector functions (IgG1e3 engineered Fc by InvivoGen, San Diego Calif.; hIgG1e3-Fc1 sequence having the sequence of human Fc (SEQ ID NO: 9) with E233P/L234V/L235A/ΔG236 and A327G/A330S/P331S substitutions. The sequence information is provided in FIG. 9 (SEQ ID NO:10-18).

This antibody (ATROSAB) was produced in CHO cells. A 25 L scale production of ATROSAB was performed in a wave system over a period of 15 days with a maximum cell density of more than 12 mio cells/mL. Purity and integrity was confirmed by SDS-PAGE analysis and size exclusion chromatography (FIG. 1a, b). ATROSAB showed strong binding to recombinant human TNFR1-Fc composed of the extracellular region of TNFR1 fused to the human IgG1 Fc region (FIG. 1c). The parental antibody, H398, exhibited an identical binding in ELISA. The selectivity for TNFR1 was confirmed by flow cytometric analysis of ATROSAB using mouse embryonic fibroblasts (MEF) transfected with fusion proteins comprised of the extracellular domain of TNFR1 and TNFR2, respectively, fused to the intracellular domain of human Fas (TNFR1-Fas; TNFR2-Fas) (Krippner-Heidenreich et al. J. Biol. Chem. (2002) 277(46): 44155-63). In this assay, binding was only seen with MEF-TNFR1-Fas but not with MEF-TNFR2-Fas (FIG. 2a,b). Binding of ATROSAB to MEF-TNFR1-Fas was comparable to that of H398 as shown by a titration of antibody concentration (FIG. 2c). The EC50 values were approximately 0.1 nM for both ATROSAB and H398. Next we investigated species specificity with recombinant mouse TNFR1-Fc and rhesus TNFR1-Fc fusion proteins. In ELISA, binding of the two antibodies was observed for human and rhesus TNFR1-Fc, but not mouse TNFR1-Fc (FIG. 3b).

Affinity Measurements

Figure 4:
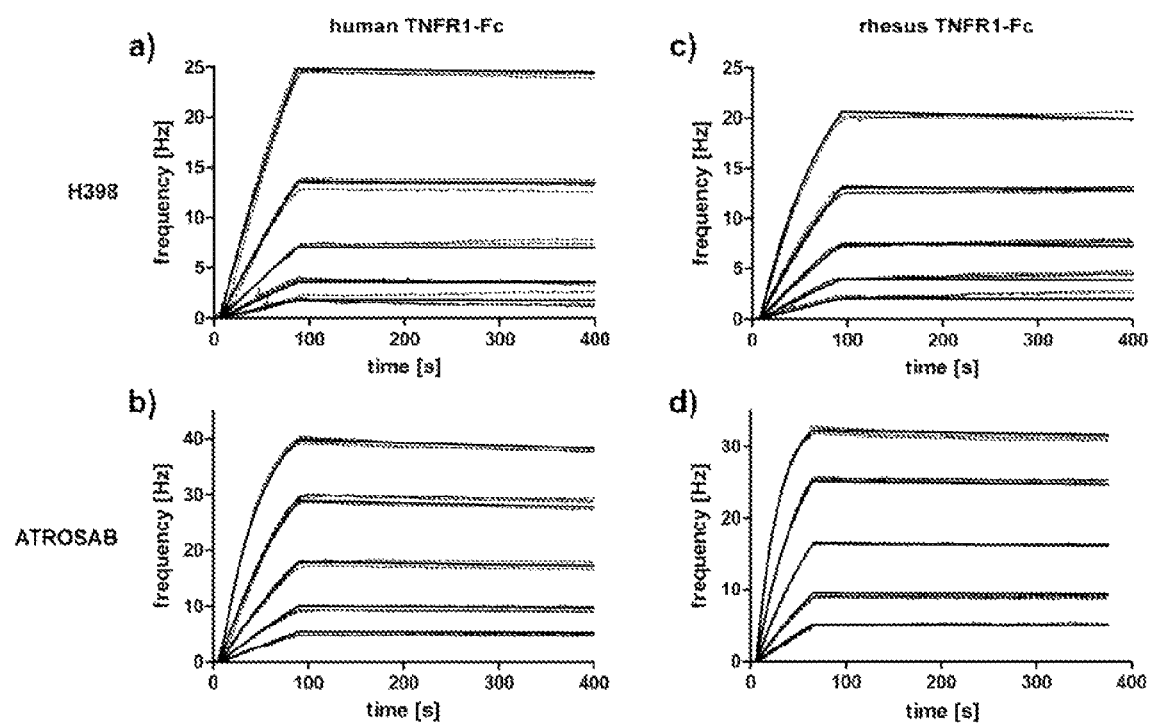

The affinity of ATROSAB for TNFR1 was determined by quartz crystal microbalance measurements using immobilized TNFR1-Fc. ATROSAB bound with sub-nanomolar affinity to human and rhesus TNFR1-Fc, similar to the affinity of H398 for human TNFR1-Fc and rhesus TNFR1-Fc (FIG. 4, Table 1). An approximately 10-fold reduced affinity was measured for monovalent scFv IZI-06.1, due to a faster off-rate, indicating that binding of ATROSAB and H398 to the dimeric TNFR1-Fc fusion proteins is influenced by avidity effects.

TABLE 1

Binding kinetics of H398 and ATROSAB

| antibody | antigen | $R_{max}$ (HZ) | $k_{on}$ ($M^{-1}s^{-1}$) | $k_{off}$ ($s^{-1}$) | $K_D$ (M) |
|---|---|---|---|---|---|
| H398 | huTNFR1-Fc | 45.4 | $3.1 \times 10^5$ | $7.0 \times 10^{-5}$ | $2.3 \times 10^{-10}$ |
| H398 | rheTNFR1-Fc | 30.4 | $2.1 \times 10^5$ | $1.0 \times 10^{-4}$ | $4.9 \times 10^{-10}$ |
| ATROSAB | huTNFR1-Fc | 46.6 | $3.8 \times 10^5$ | $1.3 \times 10^{-4}$ | $3.5 \times 10^{-10}$ |
| ATROSAB | rheTNFR1-Fc | 34.9 | $6.9 \times 10^5$ | $6.7 \times 10^{-5}$ | $1.0 \times 10^{-10}$ |
| scFv IZI-06.1 | huTNFR1-Fc | 7.2 | $3.5 \times 10^5$ | $7.6 \times 10^{-4}$ | $2.2 \times 10^{-9}$ |

Antagonistic Activity of ATROSAB

Figure 6:
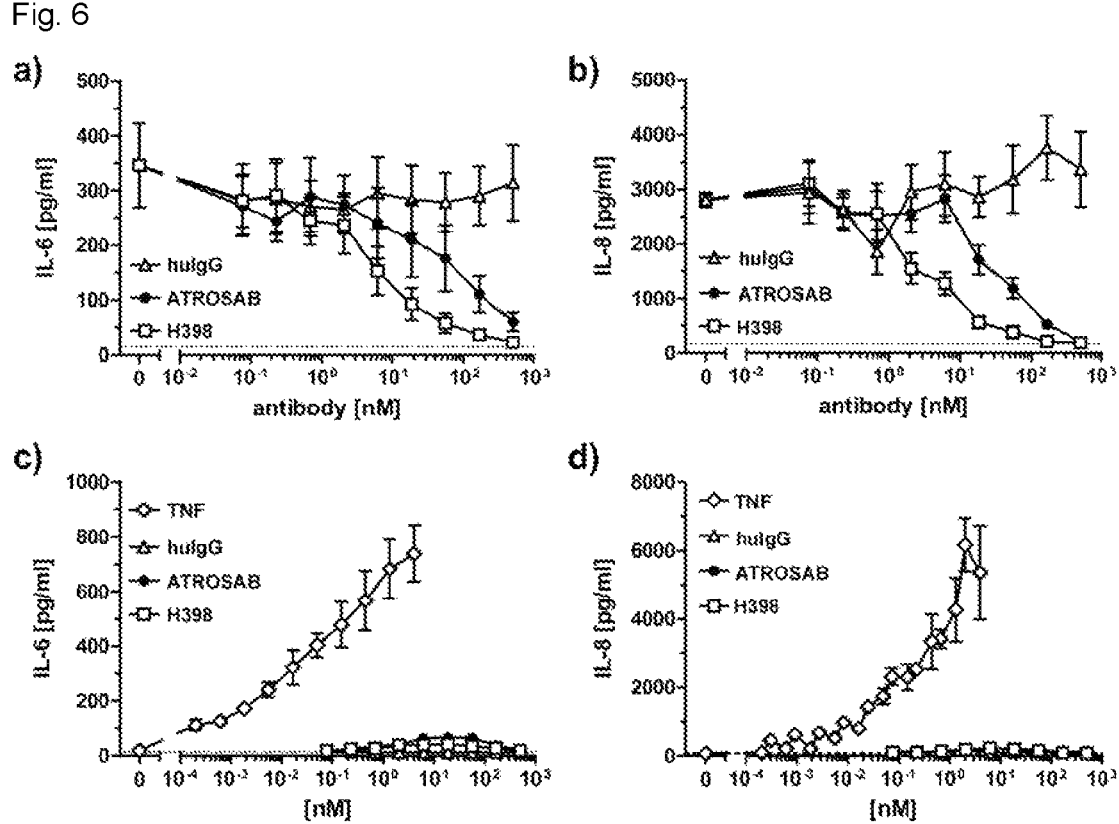

ATROSAB inhibited in a dose-dependent manner the TNF-induced apoptosis of Kym-1 cells (FIG. 5). In this assay, a TNF concentration that resulted in 90% cytotoxicity was used. About half-maximal cytotoxicity, i.e., 55% viable cells, was observed at 60 nM for ATROSAB and 8 nM for H398, respectively. We then investigated the effects of ATROSAB on TNF-induced secretion of IL-6 from HeLa cells and IL-8 from HT1080 cells, respectively. TNF induced strong secretion of IL-6 from HeLa cells in a dose-dependent manner, reaching approximately 700 pg/ml of IL-6 after incubation with 4 nM TNF (200 ng/ml) for 18 h. Similarly, TNF induced secretion of IL-8 from HT1080 cells reached approximately 7000 pg/ml after incubation with 4 nM TNF for 18 h (FIG. 6c, d). ATROSAB and H398 inhibited release of IL-6 from HeLa cells and IL-8 from HT1080 cells induced by 20 pM TNF (1 ng/ml) in a dose dependent manner (FIG. 6a, b). In these assays, the $IC_{50}$ values were 60 nM for ATROSAB and 6 nM for H398 for inhibition of IL-6 release (FIG. 6a) and for inhibition of IL-8 release (FIG. 6b), respectively. Incubation of HeLa cells or HT1080 cells (in the absence of TNF) with ATROSAB and H398, respectively, resulted in only marginal induction of cytokine release at a very narrow dose range. Only at concentrations around 10 nM, slightly elevated IL-6 levels were observed (40 to 60 pg/ml vs. 15 pg/ml of untreated cells, ie. 25-45 pg/ml induced), corresponding to 3-4.5% of the response at a comparable TNF concentration (4 nM). For IL-8, the level was increased from 80 pg/ml of untreated cells to approximately 200 pg/ml after incubation with the antibodies, corresponding to approximately 2% of the equivalent TNF response. Human IgG included as negative control had no effect on cytokine release.

Plasma Half-Life

Half-life of ATRSOAB and H398 was determined after a single dose i.v. injection into CD1 mice. Concentrations of the antibodies over a period of 7 days was measured by ELISA, i.e. detecting functional antibody molecules. Both antibodies showed a similar elimination from the blood with terminal half-lives of 10.5±2.8 d for ATROSAB (n=2) and 8.1±1.5 d for H398 (n=3) (FIG. 7).

Epitope Mapping

Because H398 and ATROSAB do not bind to mouse TNFR1, we applied a domain swapping strategy for epitope mapping (FIG. 8). Binding to these chimeric TNFR1-Fc molecules was analyzed by ELISA. All constructs were capable of binding human TNF, although constructs 3 and 4 showed a slightly reduced binding compared with the other constructs, nevertheless demonstrating that the chimeric molecules retained ligand-binding activity. No binding of ATROSAB and H398 was seen with chimeric molecules where the human CRD1 and 2 (construct 3) or only the CRD1 was substituted by the corresponding mouse domains (construct 4). Further, no binding was seen when only the A1 domain of CRD1 of human TNFR1 was exchanged with the corresponding mouse sequence (construct 5). Binding was strongly reduced, too, with mouse TNFR1 containing the human CRD1 (construct 7) or the human A1 domain of CRD1 (construct 6), indicating that further regions are required for full binding. Extension of the human portion to include subdomain A1 of CRD2 resulted in a chimeric TNFR1 to which H398 and ATROSAB show strong binding (construct 8). Thus, the epitope resides in the N-terminal region of TNFR1 covering residues 1 to 70. Within this region, 15 residues are different between human TNFR1 and mouse TNFR1, while only one residue is different between human and rhesus TNFR1 (FIG. 8b). This residue (Ile 21) is substituted by a valine in rhesus and mouse TNFR1. Several of the residues different between human and mouse TNFR1 are exposed to the interaction site of the receptor with TNF, including Pro23, Gln24, Tyr30, Asn31, Ser57, Ser 59, His66, and His69. In order to further narrow down the epitope, we exchanged P23 and Gln24, located in sub-domain A1 of CRD1, by the corresponding mouse residues in the chimeric TNFR1 h1-2A1/m2B2-4 (construct 10, FIG. 8a,b). These mutations completely abolished binding of ATROSAB and H398 under the applied assay conditions.

Discussion

Here we describe the generation of an IgG1 derivative (ATROSAB) of a humanized TNFR1-specific antagonistic monoclonal antibody. The IgG format was chosen because of its long half-life, established production and increased binding due to bivalency. ATROSAB possesses an Fc-region deficient in activation of ADCC and CDC.

Receptor-selective inhibition by ATROSAB and the parental mouse antibody resulted in blocking of distinct signaling pathways of TNFR1, as shown by inhibition of TNF-mediated cell death and as well as NF-κB induced IL-6 and IL-8 release. Both cytokines are biomarkers of inflammation and are elevated e.g. during episodes of active disease in rheumatoid arthritis. The antagonistic activity of the murine H398 and the humanized monovalent Fab was described to be based on interference with ligand binding. By using a domain swapping strategy for chimeric mouse/human TNFR1-Fc fusion proteins, we show that the epitope recognized by ATROSAB and H398 also includes subdomain A1 of CRD2, i.e. the total epitope is covered by amino acids 1 to 70 in the N-terminal region of TNFR1. The finding that also subdomain A1 of CRD2 is required for antibody binding hints toward sterical blockage as cause for neutralization of TNF action. The structure of TNFR1 with bound TNF (FIG. 7) shows that the identified epitope region at least partially overlaps with the TNF binding site which is mainly located in CRD2 and CRD3. Additionally, site directed mutagenesis revealed that residues Pro23 and Gln24 of subdomain A1 of CRD1 directly contribute to antigen and species specificity. This is of interest as CRD1 is not directly involved in ligand binding but is critically involved in TNFR1 signaling. CRD1 controls high affinity ligand binding by stabilizing the conformation of the subsequent CRD2 and removal of CRD1 results in loss of ligand binding. In addition, CRD1 comprises a homophilic receptor/receptor interaction site, the pre-ligand-binding assembly domain (PLAD) which is essential for generation of functional TNFR signal complexes. Hence, binding of ATROSAB to CRD1 could not only displace TNF by sterical hindrance or by inducing a conformational change but could also interfere with homotypic PLAD interactions, thereby blocking the formation of functional TNFR signal complexes.

ATROSAB showed a slightly reduced antagonistic activity compared to H398 This is probably not due to altered affinity since affinities of both antibodies for recombinant human TNFR1 were similar as determined by quartz crystal microbalance measurements and in flow cytometry measurements using TNFR1-expressing cells. Currently, we cannot exclude that ATROSAB and H398 bind in a slightly different way or to a slightly different area within the identified region (aa 1-70) containing the epitope. Further epitope mapping by site directed mutagenesis of exposed residues will provide insights into the exact localization of the conformational epitope of ATROSAB and H398 and the mechanism of ligand blocking.

In absence of TNF, for both antibodies (H398 and ATROSAB) a minor stimulatory activity was revealed at a very narrow dose range by sensitive in vitro assays with established cell lines. This marginal effect of the bivalent antibodies on the cytokine release might be caused by some cross-linking of receptors, because for monovalent Fab fragments of ATROSAB and H398 in the same assays, no stimulatory activity could be discerned over a 4-log dose range. However, when compared with the cellular response to TNF treatment, this minor activity of bivalent antibodies appears negligible, amounting at peak levels to 2-5% of a genuine TNF response. Moreover, on freshly isolated human peripheral blood T cells and granulocytes, no agonistic activity of the TNFR1 specific antibodies could be discerned in the TNF-dependent cellular response models of T cell activation and $O_2$-production, respectively.

Importantly, we could demonstrate binding of ATROSAB to rhesus TNFR1 with a similar affinity as for human TNFR1, thus allowing for in vivo evaluation of ATROSAB in rhesus monkeys. The collagen-induced arthritis (CIA) model is the recognized standard for potential RA therapeutics and could be already reproducibly induced in rhesus macaques. Because of the well-established proximity (physiological, anatomical, genetic, microbiological and immunological) with humans, CIA in rhesus monkeys represents a very useful preclinical model for evaluation of safety and efficacy of novel therapies and enables the analysis of ATROSAB's neutralizing activity and safety in non human primates.

TNFR1-selective antagonist, such as ATROSAB, will permit new therapeutic options for diseases where anti-TNF therapeutics failed or even exacerbate disease progression, including multiple sclerosis, congestive heart failure, metabolic diseases (type II diabetes), cytokine release syndrome, septic shock, acute (stroke) and chronic (Alzheimer and Parkinson disease) neurodegenerative diseases. ATROSAB could be an especially useful therapeutic alternative in diseases already known to clinically respond to anti-TNF treatment and particularly in those diseases where specific blockage of TNFR1 and maintenance of TNFR2 function appears as a promising therapeutic approach.

The invention claimed is:

1. An anti-human tumor necrosis factor receptor 1 (anti-huTNFR1 antibody of the IgG1 type having a modified Fc region deficient in mediating effector function, wherein the antibody is a full length human or humanized IgG1 antibody.

2. The antibody of claim 1, wherein the Fc region comprises a mutation to downmodulate the effector function.

3. The antibody of claim 2, wherein the Fc region is glycoengineered to downmodulate the effector function.

4. The antibody of claim 1, wherein the Fc region comprises a heavy chain with at least one mutation selected from the group consisting of E233P, L234V, L235A, A327G, A330S and P331S.

5. The antibody of claim 1, wherein the antibody binds specifically to an epitope comprising the membrane-distal cardiolipin synthase 1 (CRD1) of huTNFR1 and subdomain A1 of cardiolipin synthase 2 (CRD2) of huTNFR1.

6. The antibody of claim 1, wherein the antibody binds specifically to an epitope represented by amino acids 1 to 70 in the N-terminal region of huTNFR1.

7. The antibody of claim 1, wherein the antibody binds specifically to the epitope recognized by the H398 antibody.

8. The antibody of claim 1, wherein the antibody binds specifically to huTNFR1 by at least two binding sites.

9. The antibody of claim 1, wherein the antibody is a humanized H398 antibody.

10. A pharmaceutical preparation comprising an antibody according to claim 1 and a pharmaceutically acceptable carrier.

11. The antibody of claim 1, wherein the antibody is produced by a recombinant mammalian expression system.

12. The antibody of claim 11, wherein a Chinese hamster ovary (CHO) production cell line is employed to produce the antibody.

13. A method of treating a condition already known to clinically respond to anti-TNF comprising the step of administering a therapeutically effective amount of an anti-huTNFR1 antibody of the IgG1 type to a patient in need thereof.

14. The method of claim 13, wherein the antibody is administered after anti-TNF or a non biologic disease modifying antirheumatic drug (DMARD) therapeutics has been administered to the patient and has not been effective in treating the condition.

15. The method of claim 13, wherein the condition is an autoimmune disease selected from the group consisting of rheumatoid arthritis, psoriasis, psoriatic arthritis, juvenile arthritis, ankylosing spondylitis, Crohn's disease and multiple sclerosis.

16. The method of claim 13, wherein the condition is Alzheimer's disease, or Parkinson's disease Alzheimer's disease or Parkinson's disease.

* * * * *